United States Patent
Freeman et al.

(10) Patent No.: US 12,343,130 B2
(45) Date of Patent: Jul. 1, 2025

(54) SPACING OF ELECTRODES FOR BIOIMPEDANCE MEASUREMENTS

(71) Applicant: Respiratory Motion, Inc., Waltham, MA (US)

(72) Inventors: Jenny Freeman, Weston, MA (US); Jordan Brayanov, Medford, MA (US); Mark H. Strong, Dover, MA (US); Nicholas Aranow, Dedham, MA (US)

(73) Assignee: Respiratory Motion, Inc., St. Louis, MO (US)

( * ) Notice: Subject to any disclaimer, the term of this patent is extended or adjusted under 35 U.S.C. 154(b) by 0 days.

(21) Appl. No.: 16/002,635

(22) Filed: Jun. 7, 2018

(65) Prior Publication Data

US 2018/0279903 A1 Oct. 4, 2018

Related U.S. Application Data

(63) Continuation-in-part of application No. 14/021,939, filed on Sep. 9, 2013.

(Continued)

(51) Int. Cl.
*A61B 5/05* (2021.01)
*A61B 5/00* (2006.01)
(Continued)

(52) U.S. Cl.
CPC ............ *A61B 5/053* (2013.01); *A61B 5/0002* (2013.01); *A61B 5/282* (2021.01); *A61B 5/296* (2021.01);
(Continued)

(58) Field of Classification Search
CPC .. A61B 5/04; A61B 5/05; A61B 5/053; A61B 5/08; A61B 5/083; A61B 5/087;
(Continued)

(56) References Cited

U.S. PATENT DOCUMENTS

| 3,433,217 A | 3/1969 | Rieke |
| 3,690,143 A | 9/1972 | Day |

(Continued)

FOREIGN PATENT DOCUMENTS

| CN | 1034665 | 8/1989 |
| CN | 102065751 | 6/2015 |

(Continued)

OTHER PUBLICATIONS

Wang et al. "A Robust Electrode Configuration for Bioimpedance Measurement of Respiration" Journal of Healthcare Engineering • vol. 5 • No. 3 • 2014 p. 313-328. (Year: 2014).*

(Continued)

*Primary Examiner* — Joseph A Stoklosa
*Assistant Examiner* — Brian M Antiskay
(74) *Attorney, Agent, or Firm* — Remenick PLLC

(57) ABSTRACT

An electrode padset and a method of using the electrode padset are disclosed herein. The electrode padset is a single unit, consisting of multiple patient-contacting conductive pads arranged on a single piece of material. The padset is comprised of a plurality of conductive pads, at least one conductive pad adapted to emit an electrical signal and at least one other conductive pad adapted to receive an electrical signal, and an electrically conductive material coupling the conductive pads.

36 Claims, 23 Drawing Sheets

Related U.S. Application Data

(60) Provisional application No. 62/516,295, filed on Jun. 7, 2017, provisional application No. 61/808,509, filed on Apr. 4, 2013, provisional application No. 61/698,289, filed on Sep. 7, 2012, provisional application No. 61/698,257, filed on Sep. 7, 2012.

(51) Int. Cl.
*A61B 5/053* (2021.01)
*A61B 5/282* (2021.01)
*A61B 5/296* (2021.01)
*A61B 5/085* (2006.01)
*A61B 5/091* (2006.01)

(52) U.S. Cl.
CPC .......... *A61B 5/6823* (2013.01); *A61B 5/6833* (2013.01); *A61B 5/7221* (2013.01); *A61B 5/0006* (2013.01); *A61B 5/086* (2025.01); *A61B 5/091* (2013.01); *A61B 5/7203* (2013.01); *A61B 2503/045* (2013.01); *A61B 2560/0238* (2013.01); *A61B 2560/0475* (2013.01); *A61B 2562/0215* (2017.08); *A61B 2562/04* (2013.01); *A61B 2562/085* (2013.01); *A61B 2562/14* (2013.01)

(58) Field of Classification Search
CPC ......... A61B 5/091; A61B 5/103; A61B 5/107; A61B 2562/046; A61B 5/282; A61B 2018/00875; A61B 5/0006; A61B 5/24; A61B 5/6843; A61B 5/1118; A61B 5/259; A61B 5/6804; A61B 5/6823; A61B 5/0531; A61B 2017/00026; A61B 5/7203; A61B 2018/00755; A61B 5/6833; A61N 1/36185; A61N 1/37247; A61N 1/0534; A61N 1/0492; A61N 1/0553; A61N 1/0476; A61N 1/0484; A61N 1/3614; A61N 1/3686; A61N 1/048; A61N 1/04; A61N 1/3625
USPC ................ 600/372, 382–384, 386, 388–393, 600/508–509
See application file for complete search history.

(56) References Cited

U.S. PATENT DOCUMENTS

| | | | |
|---|---|---|---|
| 3,742,936 | A | 7/1973 | Blanie |
| 4,036,217 | A | 7/1977 | Ito |
| 5,058,583 | A | 10/1991 | Geddes et al. |
| 5,953,441 | A | 9/1999 | Setlak |
| 6,168,568 | B1 | 1/2001 | Gavriely |
| 6,173,198 | B1 | 1/2001 | Schulze |
| 6,286,806 | B1 | 9/2001 | Cocoran |
| 6,366,803 | B1 | 4/2002 | Fee |
| 6,402,697 | B1 | 6/2002 | Calkins et al. |
| 6,809,462 | B2 | 10/2004 | Pelrine et al. |
| 6,976,963 | B2 | 12/2005 | Clift |
| 7,196,317 | B1 | 3/2007 | Meissner et al. |
| 7,361,146 | B1 | 4/2008 | Bharmi et al. |
| 7,530,956 | B2 | 5/2009 | Lewicke et al. |
| 8,019,402 | B1* | 9/2011 | Kryzpow ........... A61B 5/04085 600/386 |
| 8,060,175 | B2* | 11/2011 | Rowlandson ........ A61B 5/6804 600/382 |
| 8,096,962 | B2 | 1/2012 | Palazzolo |
| 8,700,121 | B2* | 4/2014 | Erlinger ............... A61B 5/4875 600/382 |
| 8,781,551 | B2 | 7/2014 | Chetham |
| 9,060,705 | B2* | 6/2015 | Holzhacker ......... A61B 5/0536 |
| 9,439,566 | B2* | 9/2016 | Arne ................... A61B 5/0022 |
| 2002/0032383 | A1 | 3/2002 | Weil et al. |
| 2002/0099277 | A1* | 7/2002 | Harry .................. A61B 5/6831 600/301 |
| 2004/0071337 | A1 | 4/2004 | Jeung et al. |
| 2004/0123667 | A1 | 7/2004 | McGrath |
| 2005/0033198 | A1 | 2/2005 | Kehyayan et al. |
| 2005/0107719 | A1 | 5/2005 | Arad |
| 2005/0113702 | A1 | 5/2005 | Salla et al. |
| 2005/0215918 | A1* | 9/2005 | Frantz ................. A61B 5/0537 600/547 |
| 2006/0058600 | A1 | 3/2006 | Eichler |
| 2006/0070623 | A1 | 4/2006 | Wilkinson |
| 2006/0111641 | A1* | 5/2006 | Manera ................ A61B 5/318 600/513 |
| 2006/0024153 | A1 | 10/2006 | Hatlestad |
| 2006/0241506 | A1 | 10/2006 | Melker et al. |
| 2006/0241513 | A1 | 10/2006 | Hatlestad |
| 2007/0010764 | A1 | 1/2007 | Palazzolo et al. |
| 2007/0276300 | A1 | 11/2007 | Olson et al. |
| 2008/0312565 | A1 | 12/2008 | Celik-Butler et al. |
| 2009/0062672 | A1 | 3/2009 | Sly et al. |
| 2009/0149748 | A1 | 6/2009 | Lenhardt et al. |
| 2009/0264789 | A1 | 10/2009 | Molnar et al. |
| 2009/0264792 | A1* | 10/2009 | Mazar ................. A61B 5/0531 600/547 |
| 2009/0292192 | A1* | 11/2009 | Silber .................... A61N 1/048 600/372 |
| 2009/0326253 | A1 | 12/2009 | Watson et al. |
| 2009/0326353 | A1 | 12/2009 | Watson |
| 2010/0152600 | A1 | 6/2010 | Droitcour et al. |
| 2010/0228166 | A1 | 9/2010 | Centen |
| 2010/0241181 | A1 | 9/2010 | Savage et al. |
| 2010/0324404 | A1* | 12/2010 | Harrold ............... A61B 5/0295 600/509 |
| 2011/0077497 | A1 | 3/2011 | Oster |
| 2011/0118619 | A1* | 5/2011 | Burton ................ A61B 5/0476 600/544 |
| 2011/0160548 | A1* | 6/2011 | Forster ................ A61B 5/6833 600/301 |
| 2011/0245712 | A1 | 10/2011 | Patterson et al. |
| 2011/0306850 | A1 | 12/2011 | Hatlestad et al. |
| 2012/0041279 | A1 | 2/2012 | Freeman |
| 2012/0101358 | A1* | 4/2012 | Boettcher ............ A61B 5/4041 235/375 |
| 2012/0165883 | A1 | 6/2012 | Kalgren et al. |
| 2013/0023781 | A1 | 1/2013 | Freeman et al. |
| 2013/0102920 | A1 | 4/2013 | Fan et al. |
| 2013/0187941 | A1 | 7/2013 | Noon |
| 2013/0296823 | A1 | 11/2013 | Melker et al. |
| 2013/0338473 | A1* | 12/2013 | Bohorquez ............ A61B 5/053 600/393 |
| 2014/0024915 | A1* | 1/2014 | Jaakkola ............. A61B 5/0245 600/388 |
| 2014/0073895 | A1 | 3/2014 | Brayanov |
| 2015/0087950 | A1* | 3/2015 | Felix ................... A61B 5/0022 600/382 |
| 2015/0157240 | A1* | 6/2015 | Shoudy ............... A61B 5/0536 600/547 |
| 2017/0105648 | A1* | 4/2017 | Boverman ............. A61B 5/053 |

FOREIGN PATENT DOCUMENTS

| | | |
|---|---|---|
| EP | 1302217 | 4/2003 |
| EP | 2008581 | 12/2008 |
| EP | 2018825 | 1/2009 |
| JP | 2000-70370 | 3/2000 |
| JP | 2007-203041 | 8/2007 |
| JP | 2009-240752 | 10/2009 |
| WO | WO00/33733 | 6/2000 |
| WO | WO2007/064682 | 6/2007 |
| WO | WO2007/147505 | 12/2007 |
| WO | WO2008/130549 | 10/2008 |
| WO | WO 2009/03 6312 | 3/2009 |

(56) References Cited

FOREIGN PATENT DOCUMENTS

| WO | WO2009/035965 | 3/2009 |
|---|---|---|
| WO | WO2010/059049 | 5/2010 |

OTHER PUBLICATIONS

EP Office Action for PCT/US2010/047604, dated Mar. 5, 2015.
CN Office Action for Application No. 201380057998.2, dated Aug. 24, 2017.
U.S. Appl. No. 13/554,346 filed Jul. 20, 2012, Freeman.
U.S. Appl. No. 12/667,216 filed Dec. 23, 2010, Freeman.
U.S. Appl. No. 61/449,811 filed Mar. 7, 2011, Panasyuk.
U.S. Appl. No. 61/509,952 filed Jul. 20, 2011, Freeman.
U.S. Appl. No. 61/480,105 filed Apr. 28, 2011, Robinson.
PCT Search Report for PCT/US2011/47812, dated Jan. 10, 2012.
PCT Patentability Report for PCT/US2011/47812, dated Jan. 10, 2012.
PCT Patentability Report for PCT/US2008/76224, dated Mar. 16, 2010.
EP Search Report for PCT/US2011/047812, dated Feb. 19, 2014.
PCT Search Report for PCT/US2012/47604, dated Oct. 12, 2012.
PCT Patentability Report for PCT/US2012/47604, dated Oct. 12, 2012.
PCT Search Report of Nov. 10, 2008.
PCT Patentability Report of Nov. 10, 2008.
Pajic, et al., Model-driven safety analysis of closed-loop medical systems, IEEE Trans Industr Inform. vol. 10, pags. 1-35, p. 4, para. 1-2, Oct. 28, 2013.
PCT Search Report for PCT/US15/59032, dated Feb. 4, 2016.
U.S. Appl. No. 13/210,360, filed Feb. 16, 2012, Freeman.
U.S. Appl. No. 13/554,346, filed Jan. 24, 2013, Freeman.
Japenese Office Action for PCT/US2011/047812, dated Mar. 2, 2015.
EP Office Action for PCT/US2011/47812, dated Mar. 11, 2015.
Zulkarneev R Kh. Et al., A Hardware-Software System for Volumetric Calibration of Impedance Pneumograms, Biomedical Engineering, vol. 35, No. 1, 2001, pp. 48-51.
PCT Search Report for PCT/US2013/058797, dated Feb. 25, 2014.
EPO Search Report for PCT/US2013/058797, dated Jul. 16, 2016.
Search Report and Written Opinion for PCT App. No. PCT/US18/36475, dated Sep. 7, 2018.
U.S. Appl. No. 12/677,216, Freeman.
U.S. Appl. No. 13/210,360, Freeman.
U.S. Appl. No. 13/554,346, Freeman.
EPO Search Report for PCT/US2011/047812, dated Feb. 19, 2014.

* cited by examiner

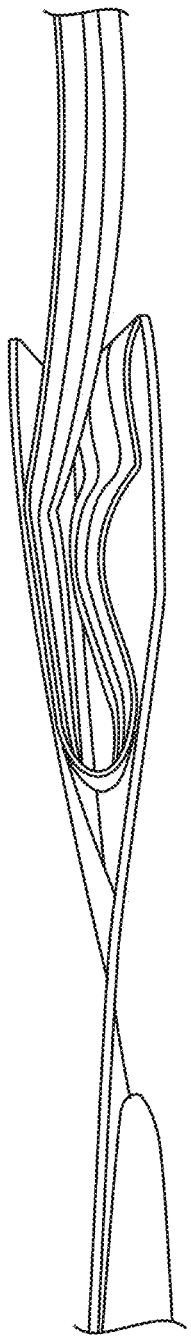
FIG. 3
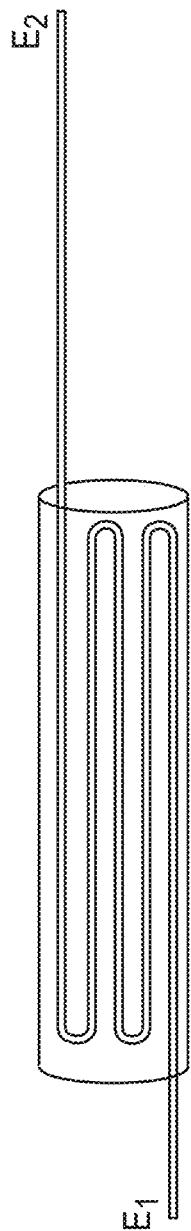
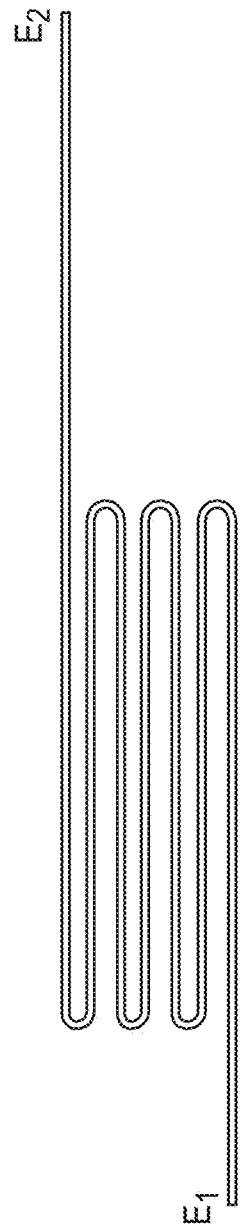
FIG. 4

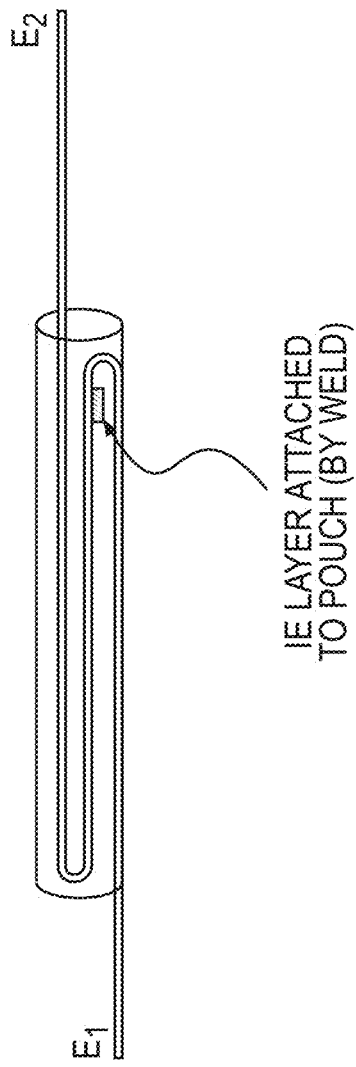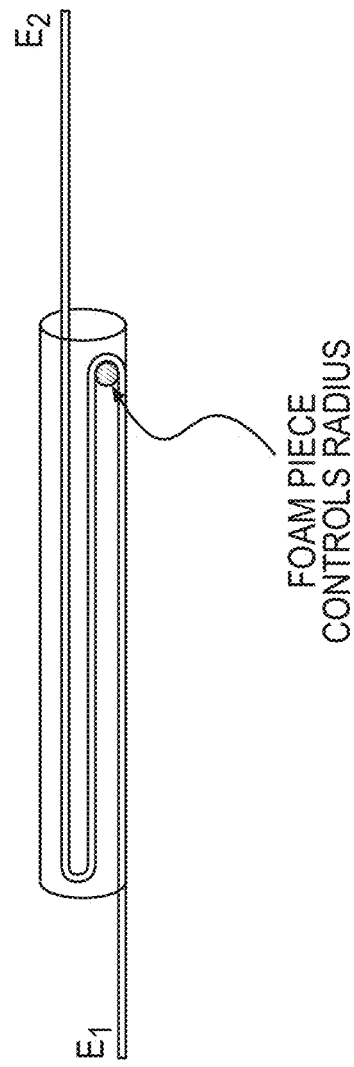

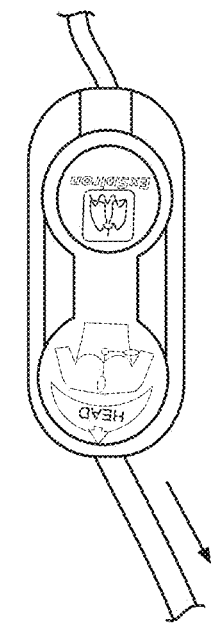
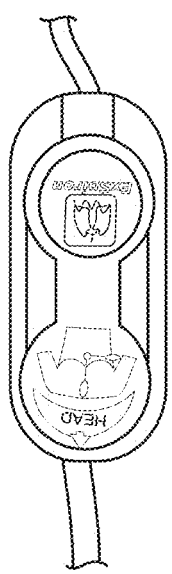
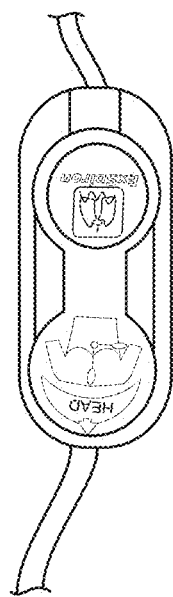
FIG. 10B
FIG. 10C
FIG. 10A

5-WIRE OPENING

3-WIRE OPENING

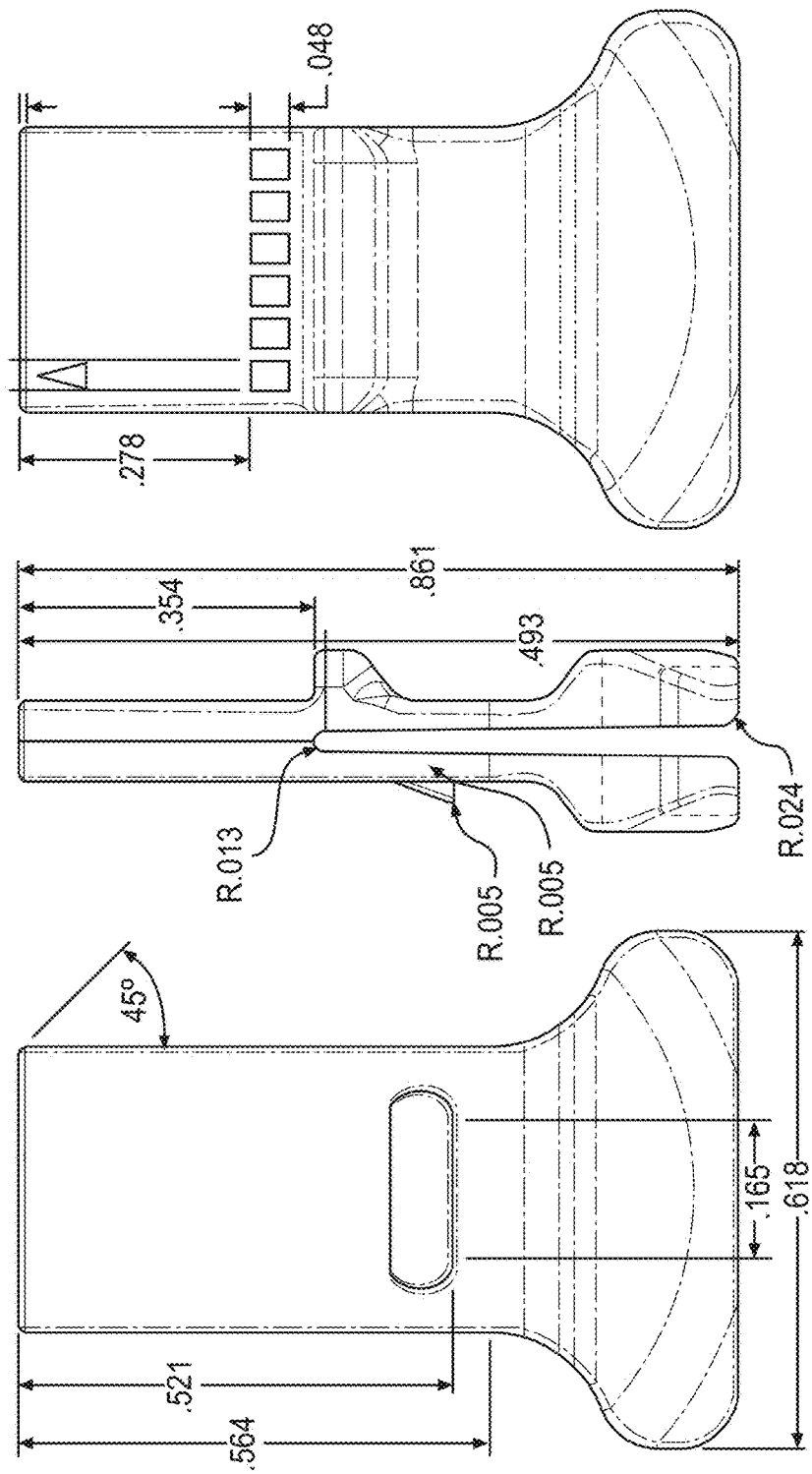
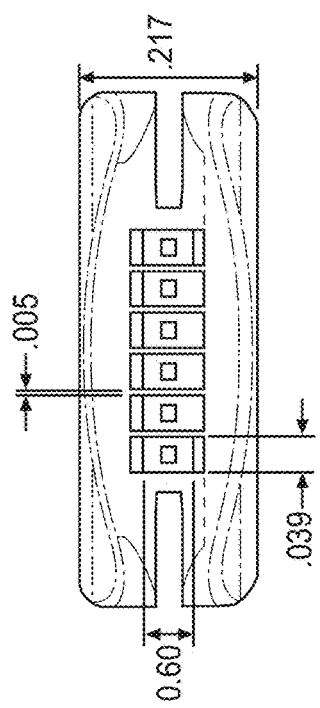
FIG. 14

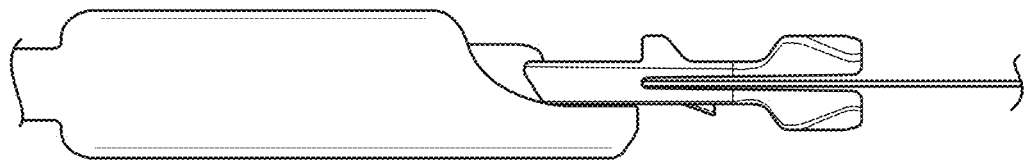
BEGINNING INSERTION
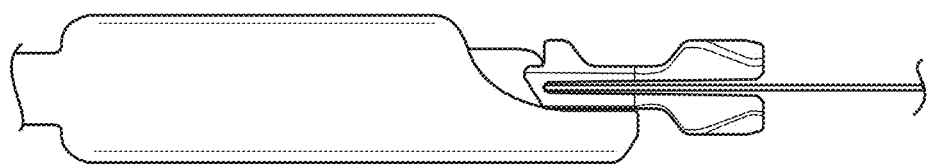
COMPLETE CONNECTION
*FIG. 16*

FIGURE 24
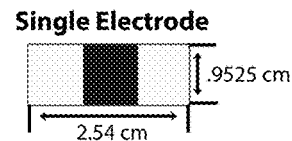
Chest Electrodes:
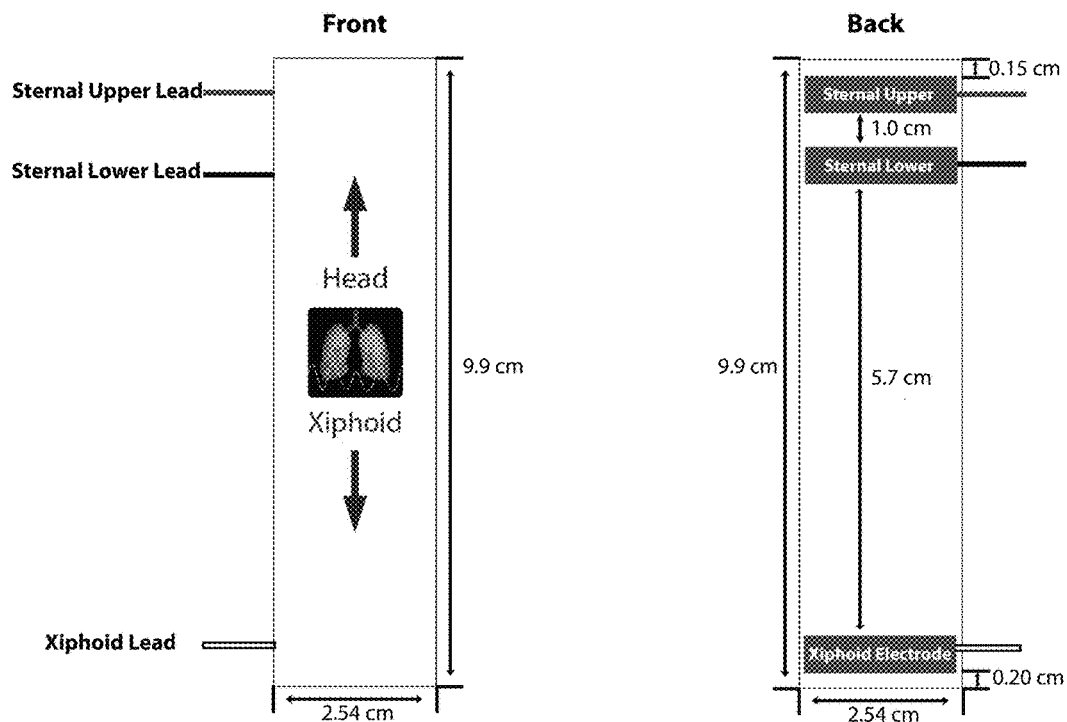
Side Electrodes:
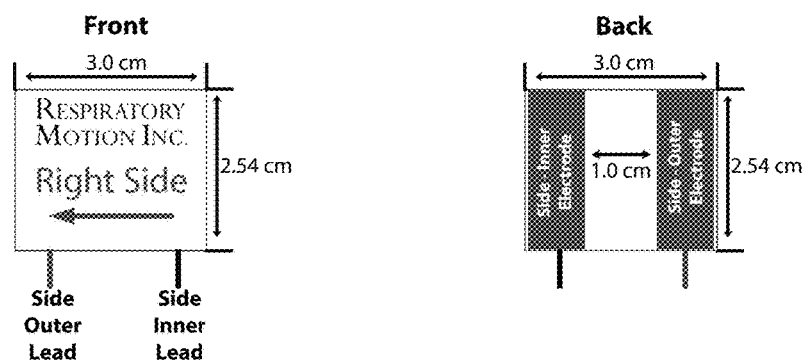

SPACING OF ELECTRODES FOR BIOIMPEDANCE MEASUREMENTS

REFERENCE TO RELATED APPLICATIONS

The present application is a continuation-in-part of Non-Provisional U.S. application Ser. No. 14/021,939, filed Sep. 9, 2013, which claims priority to Provisional U.S. Application Nos. 61/698,289 and 61/698,257, both filed Sep. 7, 2012, and 61/808,509, filed Apr. 4, 2013, all entitled "Electrode Padset." The present application also claims priority to Provisional U.S. Application No. 62/516,295, filed Jun. 7, 2017, and entitled "Spacing of Electrodes for Bioimpedance Measurements." All of which are incorporated herein in their entirety.

BACKGROUND

1. Field of the Invention

The invention is directed to electrode padsets. Specifically, the invention is directed to patient-contacting conductive pads with spacing designed to measure bioimpedance data for individuals of different sizes including adults, pediatric, neonatal and premature individuals.

2. Background of the Invention

Medical electrodes transfer the energy of ionic currents in the body into electrical currents that can be amplified, studied, and used to help make diagnoses. Medical electrodes permit surface quantification of internal ionic currents, yielding an ordinarily non-invasive test for a variety of nervous, muscular, ocular, cardiac, and other disorders that might otherwise have required surgical means to verify their presence. For instance, muscular exams using electrodes may produce evidence of diminished muscle strength and can discriminate between primary muscle disorders and neurologically-based disorders, in addition to detecting if a muscle is truly weak or seems so due to other reasons. The electrodes are typically easy to use, fairly cheap, disposable (or easily sterilized), and often unique in the tasks they help to perform. The essential role of the electrode is to provide ideal electrical contact between the patient and the apparatus used to measure or record activity.

Medical electrodes are generally comprised of a lead or wire (for conduction of electrical current), a metal electrode, and electrode-conducting paste or gel for surface electrodes. There is also often a metal (for good electrical contact) snap for the lead to snap into place so that the electrode can be disposable while the lead can be reused.

Electrodes are widely used in the healthcare field for measuring a patient's impedance. A typical electrode arrangement includes two or four electrodes interconnected in a specific pattern, secured on a patient's skin, and electrically typically connected to a microprocessor, filtering electronics, and a power source. The electrodes are often self-adhesive, with an Ag/AgCl hydro-gel structure providing an electrically conductive signal path from the skin tissue through the electrode to a measuring system. The measuring system is typically under control of a microprocessor that includes analysis software and a signal filtering module. The components measure the impedance of living tissue, including the influence of skin and body organs, based on current injected through the surface of the electrodes, in contact with skin tissue, under the control of the microprocessor. Fixed-frequency current is injected between a pair of electrodes and the resulting induced voltage is measured at another pair of electrodes, the two pairs forming a "tetrapolar" electrode set. The internal impedance is calculated as a function of the injected current and measured voltage. The operating frequency of the injected current can range from 10 Hz to over 1 MHz and the system may be able to switch between different frequencies, in order to provide additional impedance measurements and to be able to estimate both the active and reactive components of the internal impedance. Additionally, the system is capable of using may use different current levels over multiple frequencies to facilitate more accurate impedance measurements.

The filtering circuitry can be multi-staged with a first stage comprised of either a voltage follower or other means of ensuring high input impedance into the measurement circuitry, the voltage follower's output is input to a second stage, which is either a low-pass, high-pass, or a band-pass filter configured to operate in the 10 Hz to 1 MHz range in accordance with the frequency of the injected current. The incoming analog signal is then converted into a digital signal via one or more analog-to-digital (A/D) converters, making it usable by the microprocessor. The microprocessor contains input/output functionality such as RS232, Ethernet or Bluetooth and may be connected to capacitive touch screen, keyboard input, LCD screen output, additional A/D signal converters, a second CPU containing an arithmetic logic unit (ALU), RAM, or ROM memory.

In some systems, the microprocessor contains a real-time operating system with interrupt processing that, in combination with a secondary CPU processes the output of the A/D converter and generates a measurement on the internal impedance. The CPU processes the digital signal or impedance using the analysis software. Prior to operation the input function, a keyboard or touch screen, can accept patient information such as weight, torso size, height or age, or the information can be stored in ROM.

Typically, the measuring electrodes are placed on the patients' skin in a two or four electrode configuration. The four-electrode configuration helps reduce or even eliminate the effects of skin impedance over the two-electrode configuration. In today's medical practice, electrode selection is important. A variety of electrodes are designed for different populations, for example neonates, pediatrics, premature infants, or adults. Also, positioning of the electrodes on a patient's body can influence impedance measurements. The measurements may be influenced by anatomical features (e.g. scar tissue, skin lesions, etc.), body composition (body fat versus muscle), or body habitus (barrel chested vs. skinny vs. abdominal obese or high BMI patients). In the case of neonate or premature infant versus an adult, the distance between electrode pairs changes as the trans-thoracic cavity size differs considerably, but the distance between electrodes within a pair (source-sense) must also change to accommodate size.

It is common practice to use a Kelvin (4-wire or tetrapolar) electrode configuration when performing impedance measurements. This configuration consists of a pair of source electrodes and another pair of sense (or sink) electrodes. Typically, the spacing between the source and sense electrodes is not considered integral to the impedance measurement and in fact source and sync electrodes are often treated as co-incidental.

In the four-electrode configuration or tetrapolar sensor configuration, a pair of sensors or electrodes are used to inject (i.e. source) known current at a known frequency or frequencies into the body, and a separate pair of electrodes measure induced voltage across a patient's body. The current electrodes are sometimes called "excitation electrodes" and the voltage electrodes are sometimes called "sense electrodes". Changes in the spacing between a pair of sense and source electrodes can affect the measured impedance.

Given the known current and measured voltage, the impedance is determined from Ohm's Law impedance "Z", equals voltage "V" divided by current "I". Impedance has a real and imaginary component. $Z=I+/-J$, where I is the magnitude of the real component and J is the magnitude of the imaginary component (sometimes called the dynamic component). The phase angle of the impedance is arctan(I/J). The angle sometimes used for the filtering system amplifiers.

SUMMARY OF THE INVENTION

The present invention overcomes the problems and disadvantages associated with current strategies and designs and provides new tools and methods of measuring physical parameters of a patient.

One embodiment of the invention is directed to a system for measuring bioimpedance signals. The system comprises an electrode padset, a microprocessor adapted to be in communication with and receive bioimpedance signals from the electrode padset and measure the bioimpedance of the patient and a parasitic impedance mitigation system. The electrode padset comprises a pair of sternal electrodes, a pair of side electrodes, a xiphoid electrode, and an electrically conductive material coupling the pair of sternal electrodes and the pair of side electrodes to the xiphoid electrode.

Preferably, there is a first distance between the pair of sternal electrodes and a second distance between the pair of side electrodes. The parasitic impedance mitigation system is preferably a pad support substrate adapted to fix at least one of the first distance and the second distance at a predetermined distance to eliminate parasitic impedance. Preferably, the predetermined distance is at least 35 mm.

In a preferred embodiment, the parasitic impedance mitigating system is software executing on the microprocessor, wherein the software compensates for the parasitic impedance. Preferably, the first and second distances are known, parasitic impedance caused by the first and second distances are known, and the software is programmed to remove the known parasitic impedance. Preferably, there are a plurality of electrode padsets the microprocessor is adapted to determine which of the electrode padsets is in communication with the microprocessor. In a preferred embodiment, the software adjusts to remove the known parasitic impedance based on which electrode padset is in communication with the microprocessor. Preferably, the microprocessor determines a level of parasitic impedance and at least one of reports the determined level of parasitic impedance and stops displaying impedance measurements or secondary derived impedance measurements.

Preferably, the microprocessor outputs respiratory volume measurements. The electrode padset is preferably adapted to fit a neonate. In a preferred embodiment, the electrode padset is one of directly coupled to the microprocessor or is in wireless communication with the microprocessor. Preferably, the electrode padset is a single unit. The electrode padset is preferably adapted to acquire at least one of electrical bioimpedance (thoracic or cardiac), electrocardiography (ECG), electroencephalography (EEG), and electromyography (EMG) signals. Preferably, the electrode padset is adapted to acquire at least one channel of tetrapolar transthoracic bioimpedance signals.

In a preferred embodiment, there are at least two bioimpedance channels and the bioimpedance channels are oriented at an angle between 0 and 90 degrees to each other. Preferably, the electrode padset is adapted to acquire a bilateral transthoracic bioimpedance signal. Preferably, the electrode padset further comprises a memory chip. The memory chip preferably stores at least one of calibration data, production data, patient data, expiration date data, and electrode padset data. In a preferred embodiment, the memory chip is capable of wireless communication. Preferably, memory chip is passive and is couplable to an internal or external power supply.

Another embodiment of the invention is directed to a method of obtaining a bioimpedance signal. The method comprises selecting a padset for use on a patient, coupling the padset to a microprocessor, selecting software based on the selected padset, wherein the software is adapted to remove parasitic impedance of the padset based on the padset's geometry, delivering a current to the patient via the padset, receiving the current from the patient via the padset, filtering out the parasitic impedance, determining the impedance of the patient, calculating at least one respiratory volume measurement of the patient, and outputting the calculating at least one respiratory volume measurement of the patient.

Preferably, the microprocessor autodectects the selected padset. The method preferably further comprises informing the microprocessor of the selected padset. The method preferably further comprises inputting patient information into the microprocessor. Preferably, each respiratory volume measurement is one of tidal volume or minute volume.

Each padset is preferably comprised of a pair of sternal electrodes, a pair of side electrodes, a xiphoid electrode, and an electrically conductive material coupling the pair of sternal electrodes and the pair of side electrodes to the xiphoid electrode. Preferably, the padset's geometry comprises a first distance between the pair of sternal electrodes and a second distance between the pair of side electrodes. In a preferred embodiment, the first and second distances are known, parasitic impedance caused by the first and second distances are known, and the software is programmed to remove the known parasitic impedance. The method preferably further comprises determining a level of parasitic impedance and at least one of reporting the determined level of parasitic impedance and stopping displaying the at least one respiratory volume measurement.

Preferably, each padset is adapted to fit a neonate. Preferably, each padset is one of directly coupled to the microprocessor or is in wireless communication with the microprocessor. In a preferred embodiment, each padset is a single unit. Each padset is preferably adapted to acquire at least one of electrical bioimpedance (thoracic or cardiac), electrocardiography (ECG), electroencephalography (EEG), and electromyography (EMG) signals. Each padset is preferably adapted to acquire at least one channel of tetrapolar transthoracic bioimpedance signals.

Preferably, there are at least two bioimpedance channels and the bioimpedance channels are oriented at an angle between 0 and 90 degrees to each other. In a preferred embodiment, each padset is adapted to acquire a bilateral transthoracic bioimpedance signal. Each padset preferably comprises a memory chip. Preferably, the memory chip stores at least one of calibration data, production data, patient data, expiration date data, and padset data. Preferably, the memory chip is capable of wireless communication. In a preferred embodiment, memory chip is passive and is couplable to an internal or external power supply.

Other embodiments and advantages of the invention are set forth in part in the description, which follows, and in part, may be obvious from this description, or may be learned from the practice of the invention.

DESCRIPTION OF THE DRAWING

The invention is described in greater detail by way of example only and with reference to the attached drawing, in which:

FIG. 3 depicts an embodiment of a printed film folded twice within a pouch.

FIG. 4 depicts embodiments of a printed film folded multiple times within a pouch.

FIG. 5 depicts an embodiment of a printed film welded to a pouch.

FIG. 6 depicts an embodiment of a printed film with a folding guide device.

FIGS. 10a-c depict an embodiment of a pouch with directional openings.

FIG. 14 depicts an embodiment of a mechanical drawing of connector.

FIG. 16 depicts an embodiment of a different level of insertions of the connector and trunk cable.

FIG. 24 depicts a schematic of an embodiment the sizes separation of electrodes in the padset of FIG. 20.

DESCRIPTION OF THE INVENTION

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

It is also desirable to have a slim low-profile connector in and around the patient that does not impose any hard edges against the patient. It is also desirable to have a connection system that provides a positive snap locking connection. It is also desirable to have a connector that requires a user to squeeze the connector to allow the connector to be positively disconnected. It is also desirable to have the connector able to be disconnected when the disconnect force exceed a certain level, even when the connector is not squeezed by the user. In circumstances when a cable gets tripped over or the monitoring equipment gets moved, it is desirable to have the connection disconnect when pulled above a certain force. This disconnect force would serve to eliminate the pull on the patient and the risk of knocking the monitoring equipment over inadvertently.

In a busy hospital environment, it is possible for a healthcare worker to select and use either an expired or inappropriate padset (e.g a set of electrodes) on a patient. To address these issues, historically, hospital equipment and supplies have been carefully labeled and/or color-coded. Whereas these measures minimize the chance of a human error, they do not completely eliminate the problem. A solution is to recognize if and when a padset is inappropriately used, whether it is past its expiration date, or whether it has become faulty and communicate the problem to the end-user (healthcare provider).

With padsets of different sizes and spacing between electrodes, it is important for the padset to communicate with the monitoring device and identify the specific padset being implemented (adult vs pediatric vs neonatal vs premature infant vs large adult).

Current electrodes such as EKG can be difficult to apply and can be cumbersome when placed on the patient. Multi sensor electrodes can be difficult to apply in the correct anatomical landmarks and steps to optimize size of electrodes as related to patient size and anatomy and steps to optimize placement are required for best functionality. It is beneficial to have an electrode which can be applied to the body, is adaptable to the size of the patient, and provides for proper placement by self-alignment and graphical instructions when placed on the body.

Figure 1:
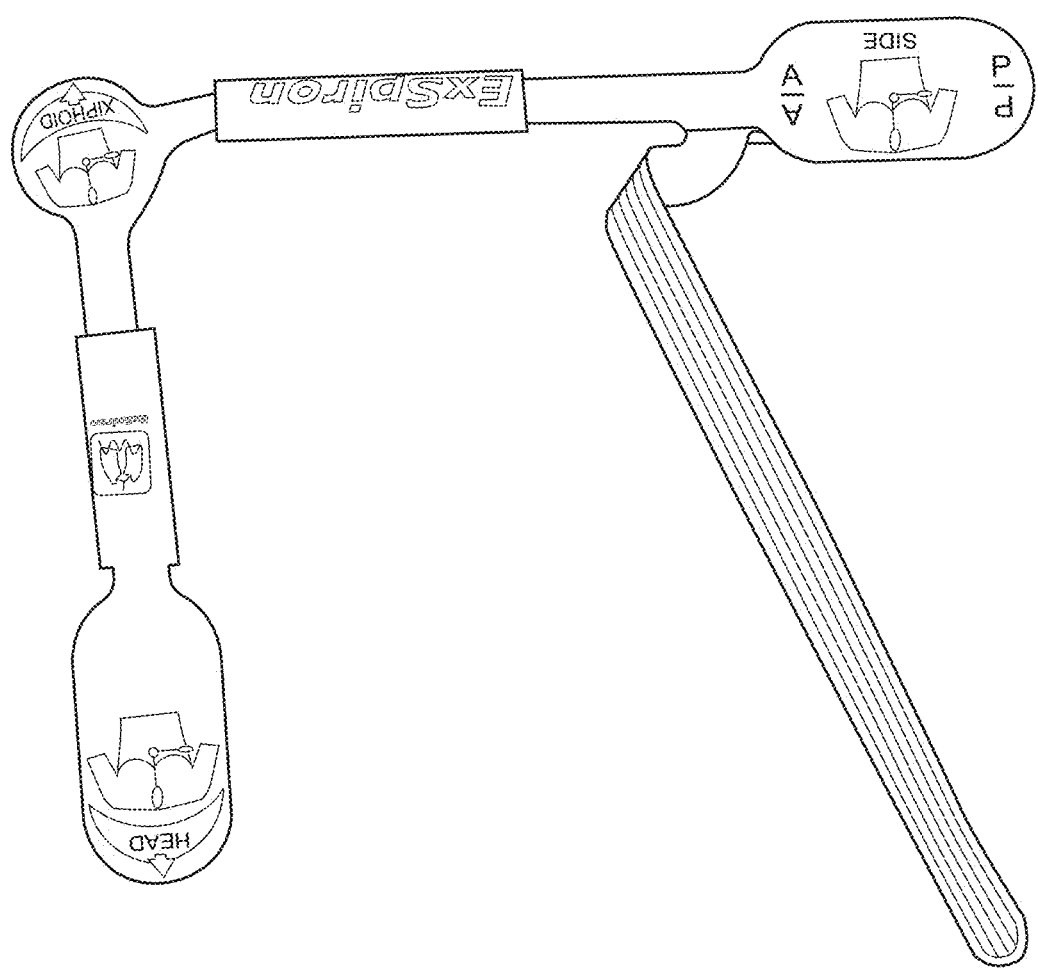
FIG. 1 is a photograph of an embodiment of an electrode of the invention.
Figure 2A:
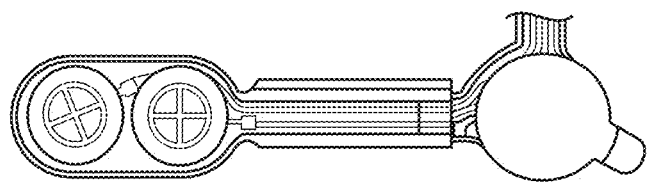
FIGS. 2a-h depict embodiments of various lengths of the electrode padset.
Figure 2B:
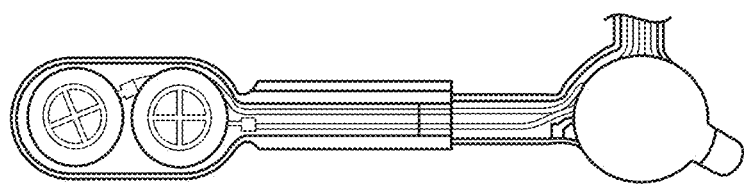
Figure 2C:
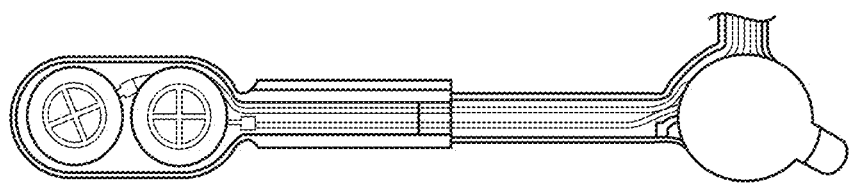
Figure 2D:
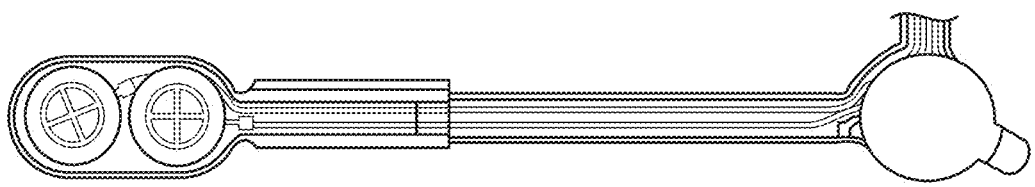
Figure 2E:
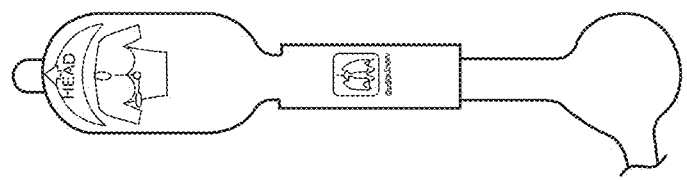
Figure 2F:
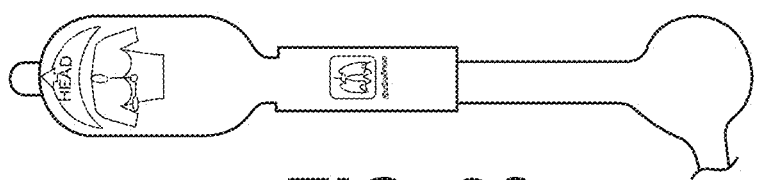
Figure 2G:
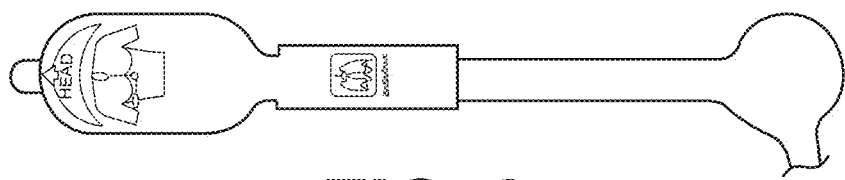
Figure 2H:
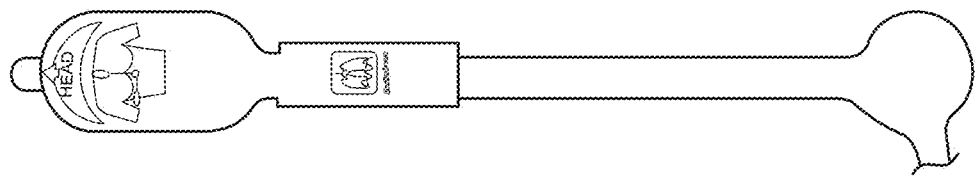

FIG. 1 depicts an embodiment of an electrode padset. The electrode padset preferably is a single unit, consisting of multiple patient-contacting conductive pads arranged on a single piece of material. In another embodiment, multiple pieces of material joined are together into a single unit. The padset is adapted to be placed on a patient in a certain configuration to acquire bioelectrical signals including but not limited to electrical bioimpedance (thoracic, cardiac or otherwise), electrocardiography (ECG), electroencephalography (EEG) and electromyography (EMG). The capability of the padset in being preconfigured in the specific electrodes location and orientation can be seen in if FIG. 1. FIG. 1 is an example of an orthogonal arrangement used for the electrode sensor array. Preferably, the padset arranges the electrodes on the patient in an anatomically relevant configuration. For example, at least one conductive pad can be coupled to a patient's mid-clavicular line, at least one conductive pad can be coupled to the patient's mid-axillary line, and at least one conductive pad can be coupled to the patient's xiphoid process. The padset can also be affixed to the patient in different configurations. In the preferred embodiment, the padset is able to attach to one or more patient trunk cables. The padset of FIG. 1 is preferably adapted for use on adults, teenagers, children, and infants above 38 kg, 45 kg, 50 kg, or above another predetermined weight or height or torso length or another relevant parameter.

Preferably, the padset includes artwork, symbols, or other indications to aid in the correct placement of the padset on the body. The portion of the padset that connects hydrogel pads is preferably made of plastic, cloth, paper, fiber, nylon, or other medical grade materials that can be sanitized and sterilized.

In one embodiment, the padset includes at least one strip of material between the electrode pads assists in anatomic placement of the pads for individuals of different sizes and body types. Preferably, the material is a vapor transmission material that allows the patient's skin to breathe and heal. In one embodiment, there is connecting paper, cloth or plastic to fix the spacing between hydrogel pairs and additional material to assist with anatomic placement of hydrogel pairs. In another embodiment, only the hydrogel pairs are connected by paper, cloth or plastic and the pairs themselves are separated into individual pair units which have only wire connections to the monitoring unit so that there is less material around the patient and instructions for proper placement is provided on the packaging for the padset. This is especially important in small or premature infants. In one embodiment, separate wires attached to each electrode or electrode pair are attached to a measuring system. For example, the material can be a cloth-like printed circuit (similar to a bandage), which is flexible and contours to the body. Preferably, the edges of the material between the electrode pads is formed (e.g. via laser cutting) to minimize sharp edges. Preferably, the edges of the material do not extend beyond the adhesive material used to affix the padset to the patient.

Figure 7:
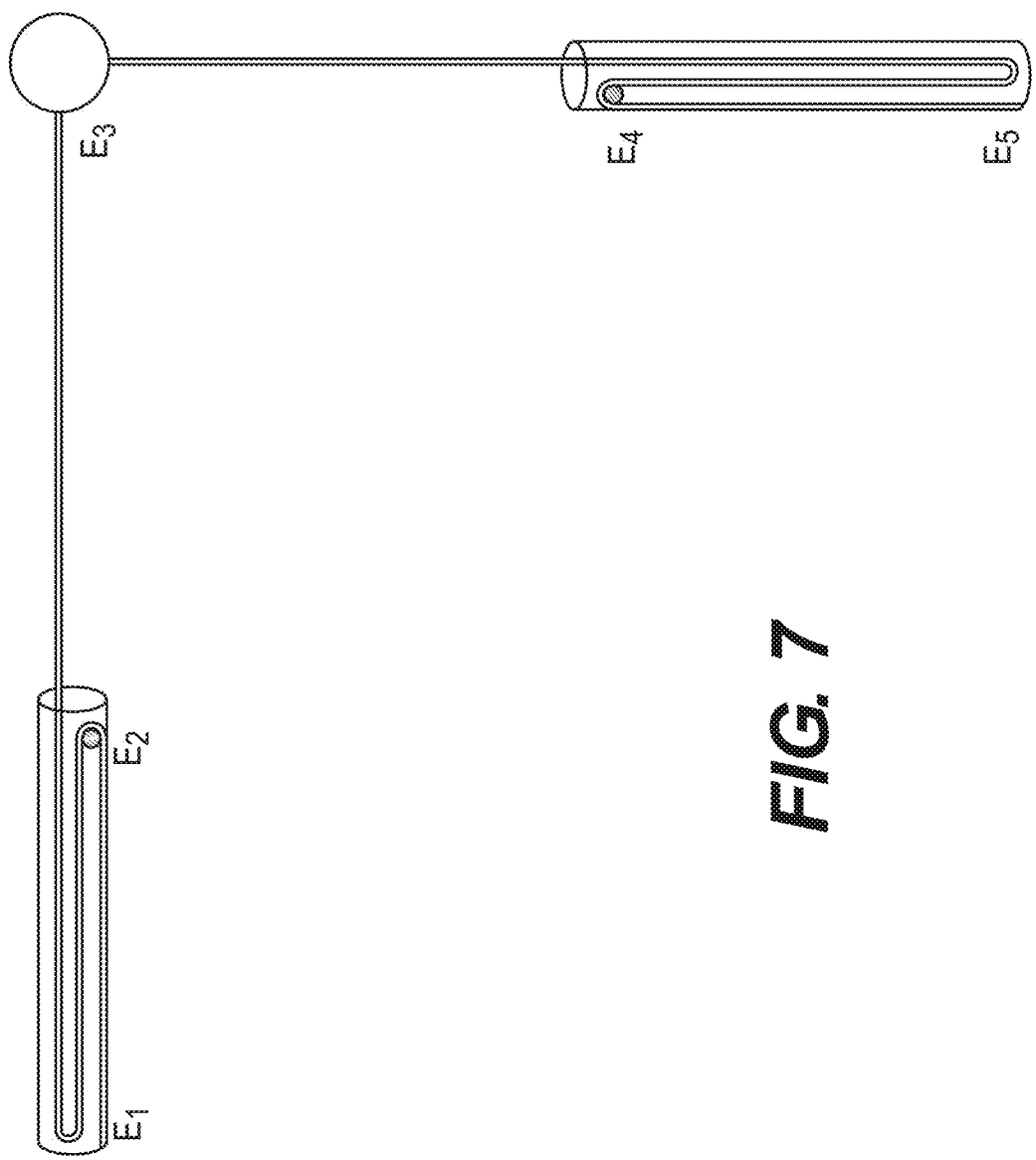
FIG. 7 depicts an embodiment of a padset with pouches positioned above the electrodes.
Figure 8:
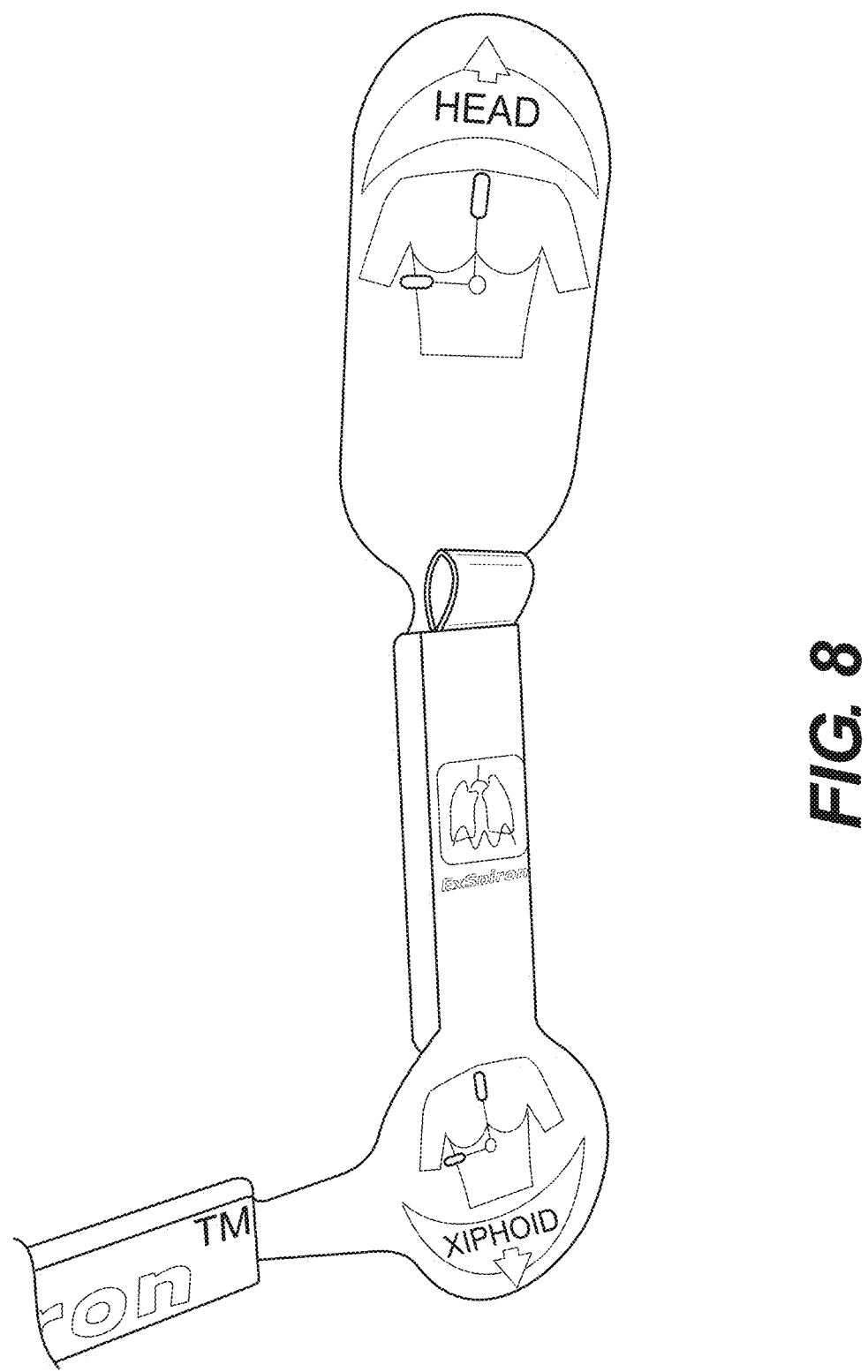
FIG. 8 depicts an embodiment of a padset with open-ended pouches.

In one embodiment, the padset is adjustable to fit different body parts. In another embodiment, the material between pads exerts a tension as it extends, but applies no tension once the user stops stretching the material. For example, the material can be elastic bands, lycra, or other stretchable materials. In another embodiment, the material between pads exerts a tension, thus holding the material close to the body. Unlike single wire cable which is flexible, low profile, and generally uses up very little space, printed film electrodes have minimal multi-directional flexibility and are therefore limited in the ability to accommodate excess length material in and around the patient. In another embodiment, the material between pads is sized to accommodate large body parts or large patients and there are provisions on the padset (e.g. pouches) to hold and contain the extra material kept the extra material out of the way. The pouch design provides for a low-profile storage of excess length material, it also automatically manages the delivery and the geometry of this material so that the material interacts with the patient in a user friendly way. Preferably, the pouch is positioned above an electrode to simplify the arrangement of the padset (see FIG. 7). Additionally, as shown in FIG. 8, the pouch can be open at both ends. Having the pouch open at both ends, allows the circuit to be stored in a non-elongated state with a gentle radius at the fold points of the material at either end of the pouch. If the fold points were maintained within the pouch, it may be possible that the material would crease at the fold points, thereby damaging the circuit.

A measuring unit can be place into or on the padset and includes the electronic components for the filtering circuitry, microprocessor, user display and input, power source, and an input module for accepting electrode measure. These components are connected to the padset via a signal path located on a flexible substrate. In one embodiment, the substrate can be a thin plastic or cloth that supports two or more conductive pathways for the signal in/out of the measuring unit to the electrodes. In one embodiment, wires can connect the padsets to the measuring unit. The electrodes may attach to the patients' skin via the hydro-gel. The measuring unit may be housed in an impact resistant case that can be secured to a hospital bed. Likewise, the measuring unit may be housed in another's medical device and interfaced via a communication protocol such as Wireless Ethernet, RFID, or Bluetooth. Preferably the padset provides information to a computerized system that delivers bioimpedance information about a patient. Most preferably the electrode padset provides information as to its size or configuration to the bioimpedance measuring system such as adult, large adult, pediatric, neonatal, premature infant, so that the bioimpedance system can select the appropriate software and/or analysis method and/or algorithm. In one embodiment, the electronic device contains a wireless communication device to pass data wireless to a receiving device.

FIGS. 2a-h depict an embodiment of the padset having a pouch to hold excess printed film. As can be seen in the figures, the printed film can be extracted from the pouch to increase the distance between the electrodes. FIG. 3 depicts a cut away view of the printed film being extracted from the pouch. Preferably, the printed film is folded several times within the pouch. For example, as shown in FIG. 3, the printed film is folded twice. However, the printed film can be folded 4, 6, or 8 times causing multiple layers of the printed film (see FIG. 4). Preferably, the printed film can be removed from the pouch to lengthen the padset and reinserted into the pouch to shorten the padset.

When extending the padset, two problems can occur. First the friction between the layers can cause instances where multiple layers of printed film are withdrawn from the pouch at the same time, instead of one layer at a time. To prevent such multiple layer withdrawal, the intermediary layer can be affixed directly to pouch at a position near the pouch exit and hold the intermediary layer directionally so it will not exit the pouch with another layer. FIG. 5, for example, depicts a pouch with the intermediary layer welded to the pouch, which also prevents a user from pulling the printed film out of the pouch completely. Secondly, folding the printed film can damage the circuit and leave it inoperable. To solve this problem the circuit's fold can be controlled at the exit of pouch by the use of a small piece of foam or other guiding device, which serves to maintain a radius to protect the printed film at folding points. The foam, as shown in FIG. 6, allows for folding the printed film back on itself without damaging the circuit.

Figure 9A:
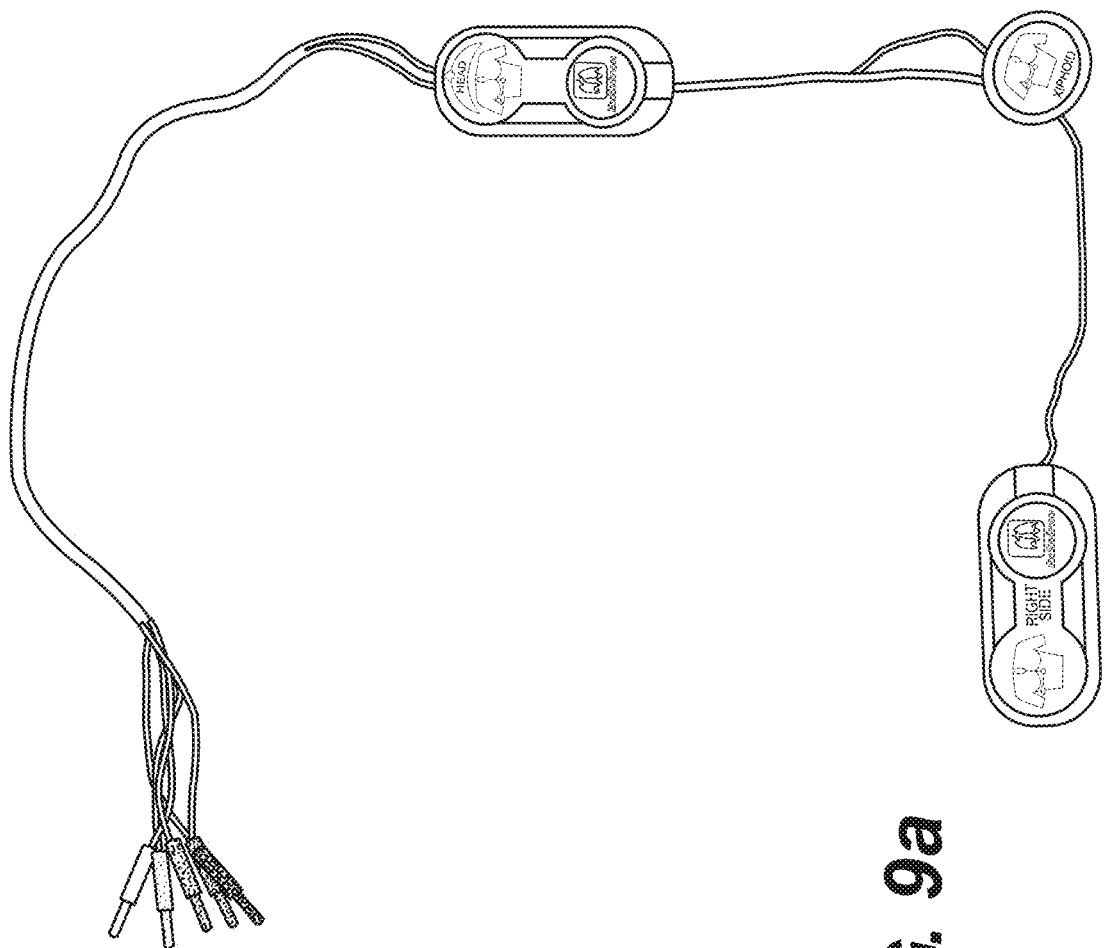
FIGS. 9a-b depict an embodiment of a padset with wire connectors.
Figure 9B:
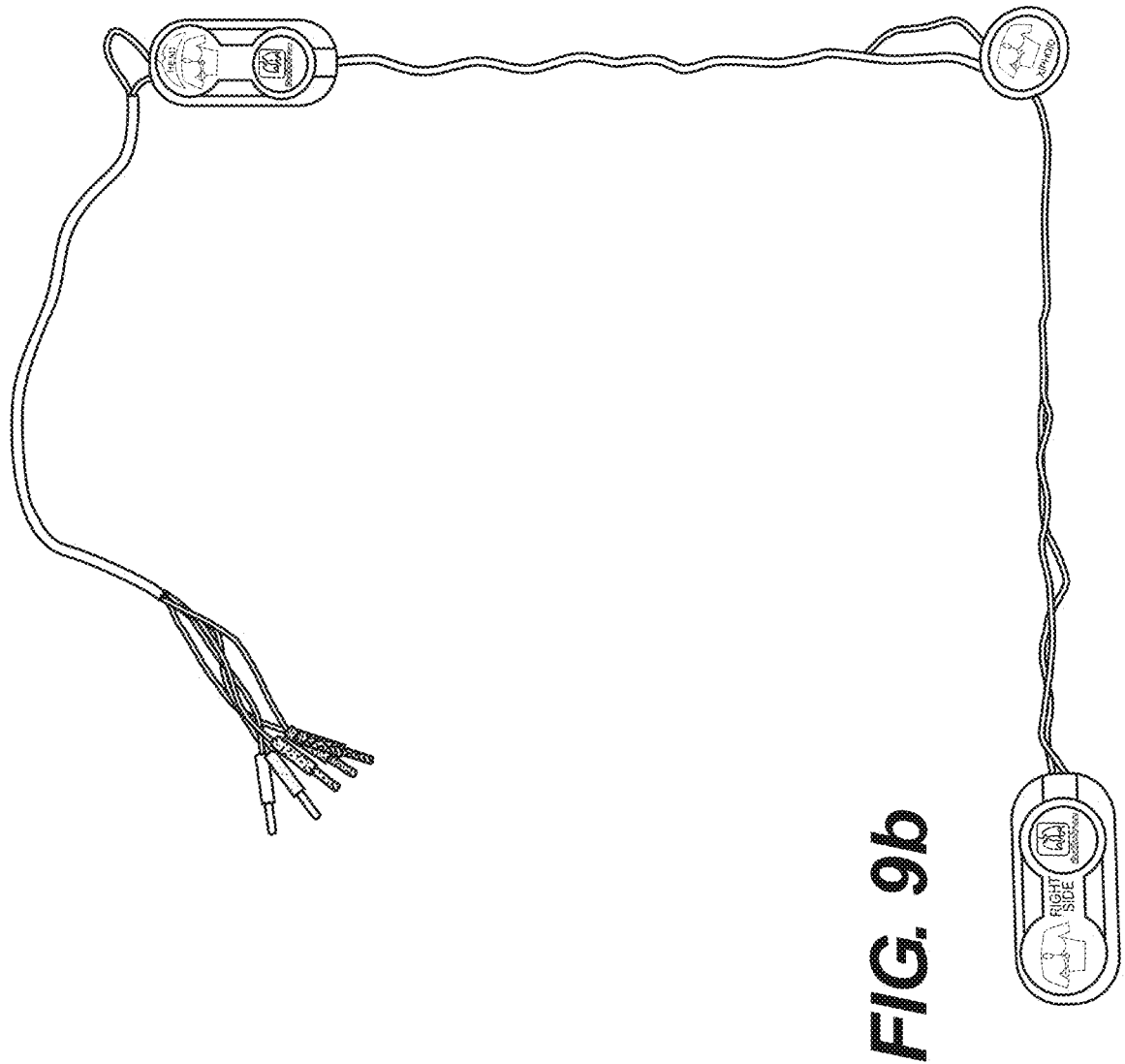
Figure 11:
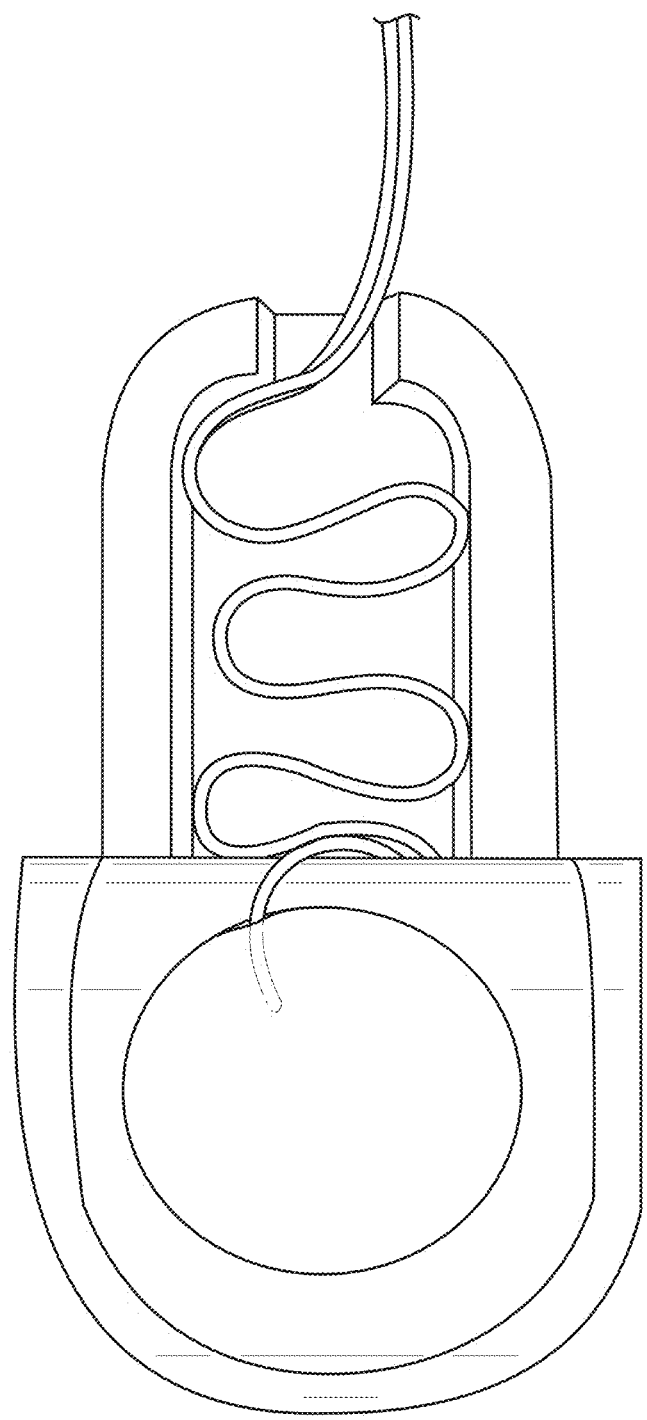
FIG. 11 depicts an embodiment of a wire in a pouch.

FIGS. 9a-b depict another embodiment of the padset. In the embodiment of FIGS. 9a-b, a wire or set of wires connects the electrodes. Preferably, a pouch or wire storage device is positioned above at least one electrode to maintain excess wire (as shown in FIG. 11). For example, in FIG. 9a, the electrodes are positioned closer together with less wire between the electrodes. Thus, the excess wire is stored in pouches positioned above the electrodes. While, in FIG. 9b, the electrodes are positioned further apart with more wire between the electrodes. The flexible, closed-cell, molded foam preferably covers the top of the double electrodes to create the pouch, and has the ability to conform to contours of the body. The double electrode at the end of the wire preferably fits around the rib cage of the patient, and is able to conform to and stick to the patient as well as house the folded wiring.

Figure 12:
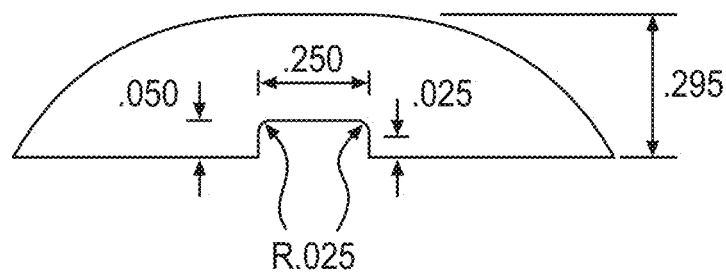
FIG. 12 depicts an embodiment of a wire opening sized to match wire size.

Additionally, as depicted by the arrows in FIGS. 10a-c, using a wire to connect electrodes allows for the wire to exit the top of the "Head" electrode with the ability to point in the right, center, or left. This is achieved, for example, by incorporating notches in the exit hole so that the nurse or care provider can position and direct the electrode lead up and away from the patient's body, for example, so that the connection from the patient's shoulder to trunk cable is safe from being pulled from patient turning in bed. The notches, or wire ports, are shown in FIG. 12. The size of the notches preferably closely matches the size of the wires and thus the notches are able to control the pushing and pulling of the wires from within the electrode.

Preferably, the wire connectors are adjustable (e.g. expandable to fit obese people) and durable. For example, a patient may be able roll over and the pouch will protect electrodes. Preferably, the wires can be routed around surgical sites. The wires are preferably able to be pushed back in the housing and have a controlled length removing from housing, (e.g. the wire does not fall out unintentionally). There may be 5, 3, or 2 wires organized in flat ribbon connected by insulation, or another number of wires. Preferably, the wires are comfortable against skin and present no sharp edges.

Figure 18:
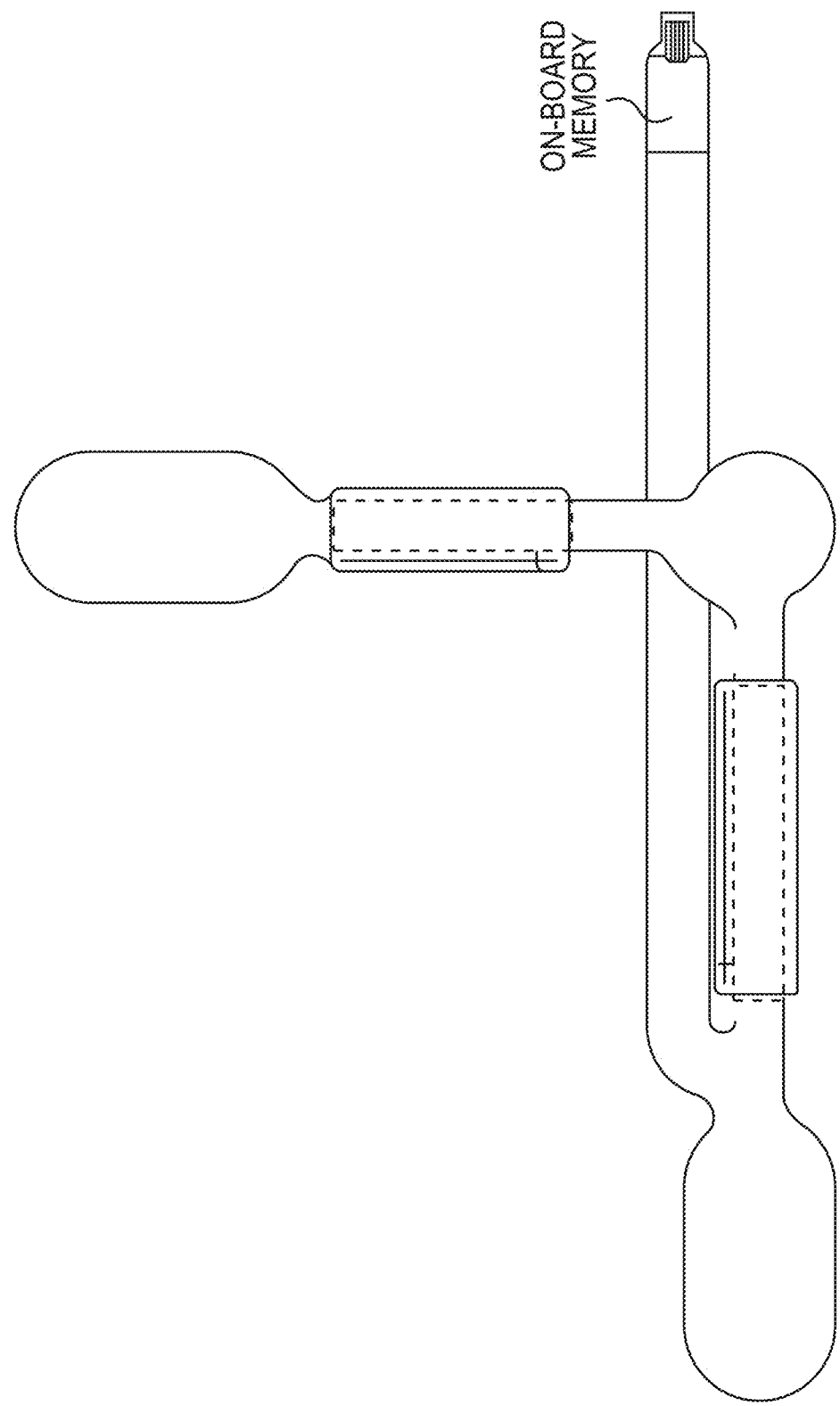
FIG. 18 depicts an embodiment of a chip installed on the backside of the padset, which is adapted to power and communicate with the chip via the connector.
Figure 19:
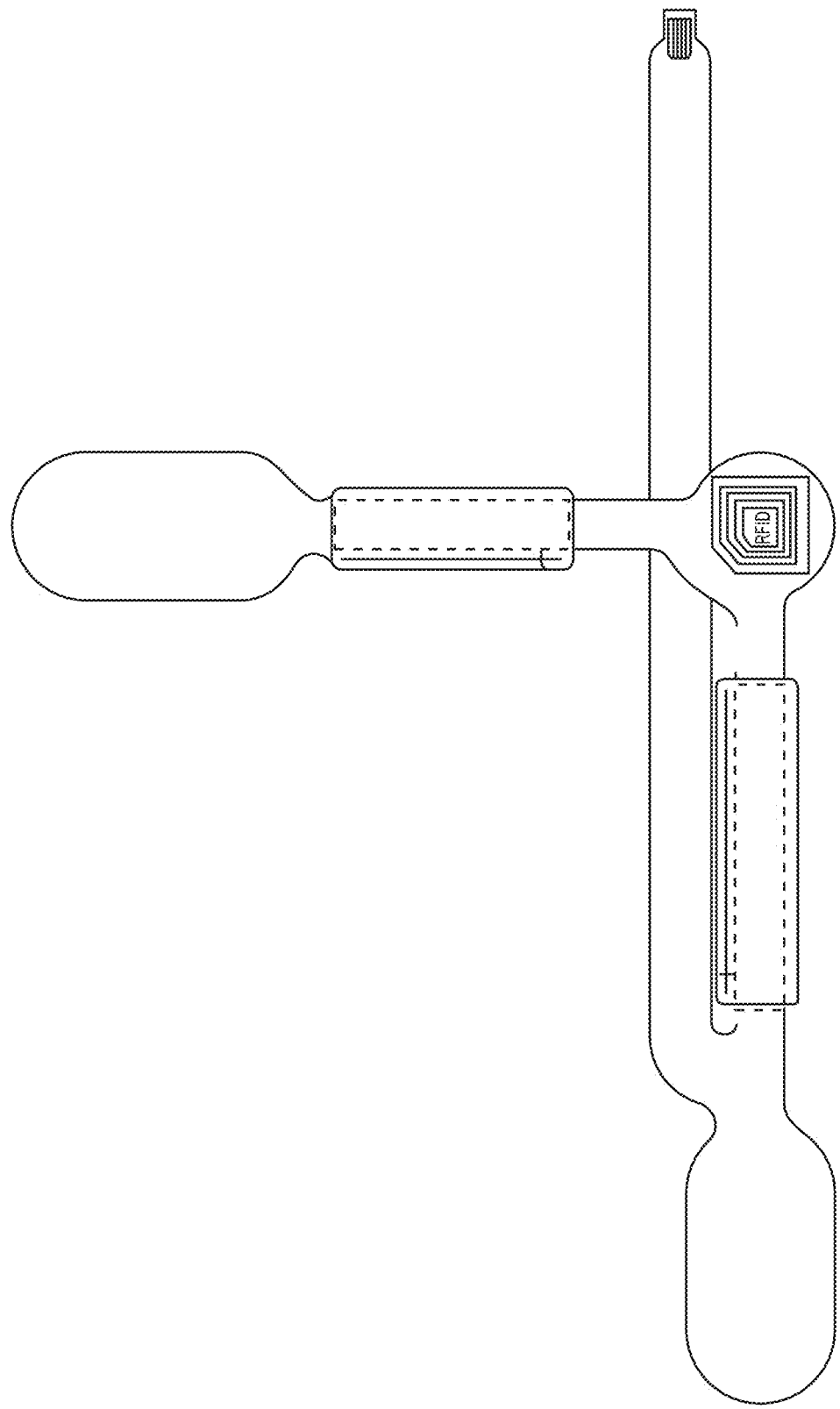
FIG. 19 depicts an embodiment of a wireless comm./memory chip (e.g. RFID) on the surface of the padset.

In another embodiment, depicted in FIGS. 18 and 19, the padset includes a memory chip containing calibration data, production data, and the like. The memory chip can be passive (e.g. RFID, SSD) or active (e.g. Bluetooth, ZigBee) and can be powered by an integrated power-cell, by the padset cable, or by a contactless inductive power source. The memory chip can be programmed with individual padset test(s) and the anticipated results from these tests. Once connected to a patient, the padset preferably communicates with the monitoring equipment and indicates what internal tests should be done and what the results should be. If there is a mismatch, a message is preferably delivered to the user. For example, in connecting a padset for normal patients to an obese patient, the padset contains information regarding the acceptable range of measured impedance and, if the readings are outside this range, the device displays an error, or, alternatively, if the padset has been outside its protective package and the exposure to air has dried out the conductive gel, the device may display an error). The internally programmed range of acceptable impedances is preferably used to identify that the memory chip can store the exact time/date when the padset was attached to a patient. After, for example, 24 hours the chip can alert the user to replace the padset.

The memory chip can store individual patient data (e.g. patient age, gender, height, weight, BMI, calibration vs. vent or spirometer) and, if unplugged from one monitoring equipment (e.g. in the OR), can immediately transfer these data to another monitor (e.g. in the PACU) assuring maximal continuity of patient care. This adaptability is useful since calibration data and equipment are not readily available to clinicians throughout the hospital.

In one embodiment, the electrode pads are arranged to acquire a tetrapolar transthoracic bioimpedance signal, where some electrode pads are used to inject a stimulating current, and others are used to read the resulting voltage. In another embodiment, the electrode pads are arranged to acquire multiple channels of tetrapolar transthoracic bioimpedance signals. This embodiment applies to configurations in which the separate channels share the same current-injecting electrodes, or have separate current-injecting electrodes. Further, the bioimpedance channels may be oriented at an angle between 0 and 90 degrees to each other.

In one embodiment, the electrode pads are arranged such that there is a primary bioimpedance channel and a secondary channel arranged at roughly a 45-degree angle. In this embodiment, the primary channel consists of two current-injecting electrodes and two voltage-sensing electrodes arranged such that the voltage-sensing electrodes sit close to an imaginary line connecting the two current-sensing electrodes. The secondary channel consists of two voltage-sensing electrodes. In one embodiment, the secondary channel has no current-injecting electrodes. In one embodiment, the secondary channel has exclusive current-injecting electrodes. In one embodiment, one of the voltage-sensing electrodes is shared between the primary and the secondary channels.

In one embodiment, the electrode pads are arranged to acquire a bilateral transthoracic bioimpedance signal. In this embodiment, both channels share one current-injecting electrode and one voltage-sensing electrode located just below the sternal notch. Each channel has its own current-injecting electrode and voltage-sensing electrode located on the midaxillary line on either side of the chest.

Figure 15:
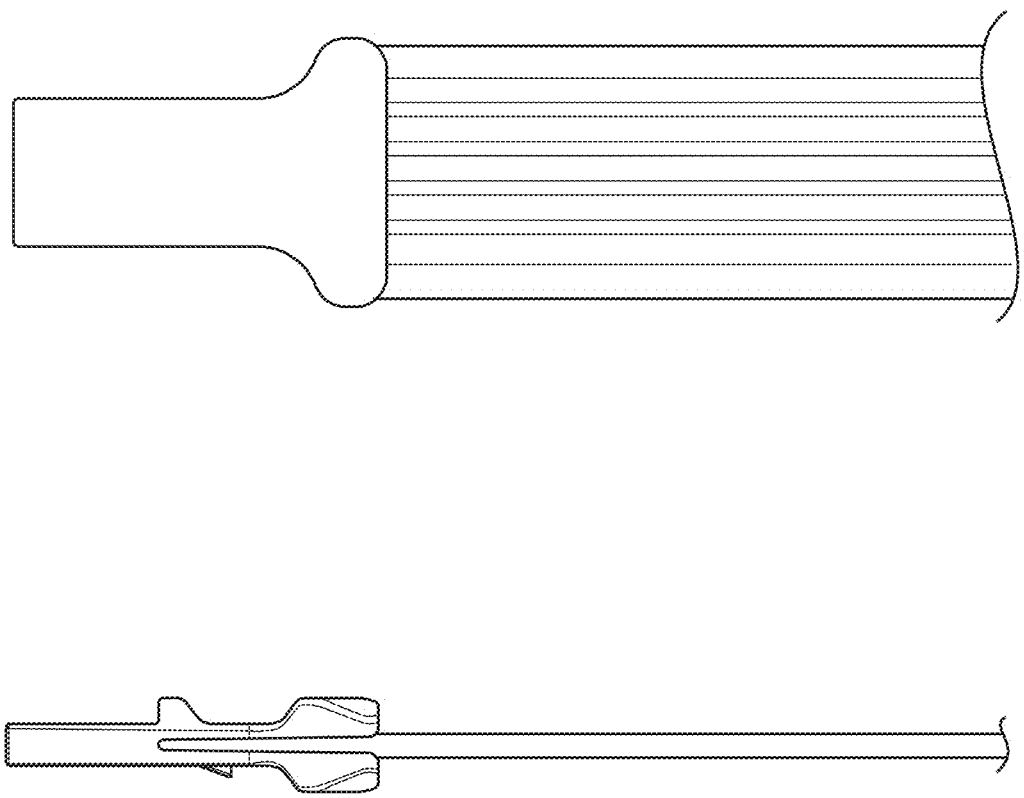
FIG. 15 depicts an embodiment of a plastic connector and traces going to electrodes.
Figure 17:
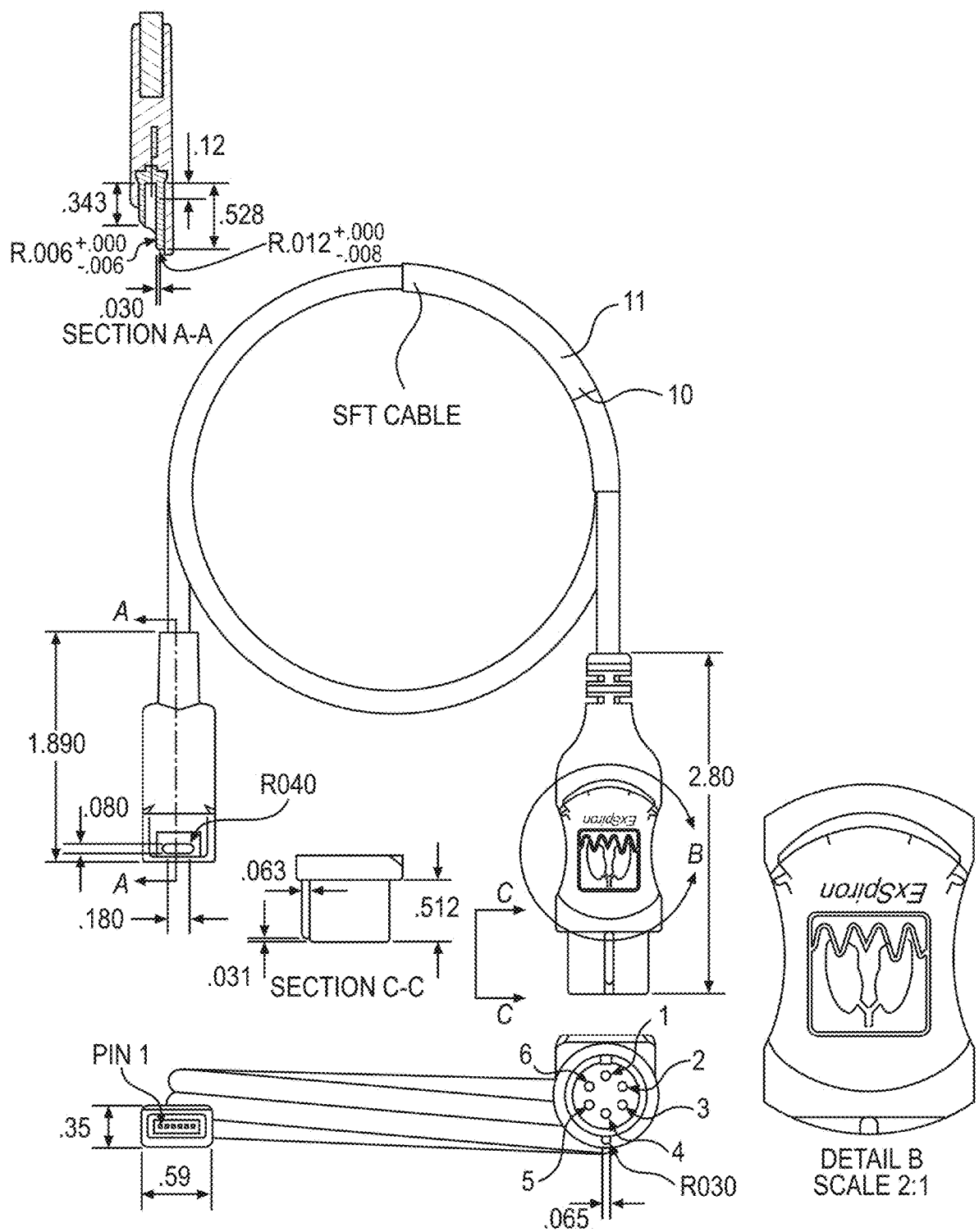
FIG. 17 depicts an embodiment of a mechanical drawing of trunk (patient) cable.

In one embodiment, the attachment method of the trunk/patient cable to the connector of the electrode padset is described. The method of attachment is preferably by pinching a plastic connector housing (shown in FIGS. 13, 14 and 15) and inserting the housing (as shown in FIG. 16) into the trunk cable connection (as shown in FIG. 17). The connection is preferably a snap connection, however other connection methods can be used. The plastic connector is preferably thin, and has a feature that snaps into a recess in the reusable trunk cable. The snap feature is preferably a small ramp protruding from the connector that slides against the trunk cable connector. During the connection process the end of the ramp, which is preferably a sharp triangular feature, engages the recess of the trunk cable, creating the click and connection. When the user's fingers are removed from the connector the two flaps preferably move away from the plastic film circuit and rest against the trunk cable connector. When the user's fingers are applied to remove the connector, the ramp feature preferably moves away from the recess and the connector can be removed.

The plastic connector is preferably a housing for the end of the circuit, and provides a space for contacts to come together in a small area. The connector is preferably a simplified single-entry point for the entire electrode padset system. The edges of all parts of the connector are preferably rounded so they do not etch away at the traces. The inside of the connector preferably has a feature that keeps the traces and contacts apart from each other. The connector preferably protects the circuit traces from damage during attachment or detachment. The connector preferably fans outward toward the electrodes, and provides more surface area for the pinching fingers to grip. The connector preferably has two engagement devices, one being the ramp described herein, and the other being a protrusion on the other side of the connector. The engagement devices preferably prevent the connection from being made if the connector is inserted in the wrong orientation.

The plastic connector preferably contains a slot where the film circuit and crimp contacts are inserted. The slot preferably also creates a space for the two ends of the connector to move towards when the device is pinched.

Figure 13:
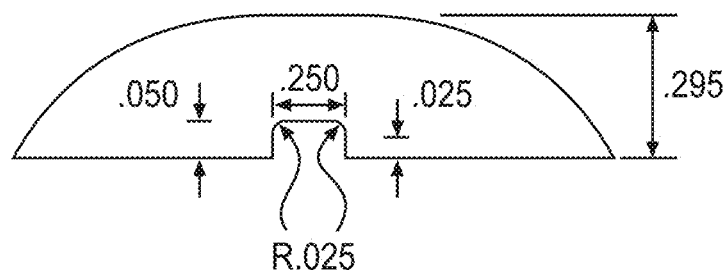
FIG. 13 depicts an embodiment of a connector.

The plastic connector preferably also provides isolation of the separate conductive elements by separating each section inside the connector (as shown in FIGS. 13 and 14). Each conductive element preferably has its own isolated compartment which provides for the necessary mechanical and electrical isolation. This isolation maintains a design which achieves a high dielectric withstand to enable the device to successfully pass a defibrillation test for medical use.

Another embodiment of the invention is a trans-thoracic impedance measurement device that has particular features based on patient size or other patient characteristics, (i.e. is smaller and suitable/optimized for pediatric or neonatal or premature infant use or larger and suitable/optimized for larger (obese) patients and a method that relies on specific distance (spacing) between sets of electrodes to ensure measurement fidelity and reduce noise. Standard adult distance between electrodes is too large to fit certain (i.e. smaller) pediatric patients, so the spacing between electrodes had to be decreased. Surprisingly, the distance between the two electrodes in each electrode set is critical to providing signal appropriate for analysis for a variety of bioimpedance measurements, including respiratory volumes. The original electrode pairs for a variety of bioimpedance monitors were designed without focus on spacing, because for normal adults, a wide range of spacings are acceptable. If the adult configuration of the device was simply "scaled down" to a pediatric size, the spacing between electrodes cannot be maintained and this leads to a degradation of the impedance measurements. If the adult configuration is reduced in size (overall footprint) while maintaining the spacing between the sets of electrodes, the resulting device is too large for the intended pediatric population. Thus, disclosed is a pediatric/neonatal/premature infant impedance measurement device which reduces the spacing between electrodes while providing a small overall footprint to fit on a small pediatric/neonatal/premature infant individual. One embodiment of the invention comprises 1) a device that implements an optimized distance between electrodes and geometry for small pediatric individuals and 2) a method of using this device.

In Respiratory Volume Monitoring (RVM) application of these sense and source electrodes at the end of the device under test (DUT) have been typically held in common and are, by design, separated by a distance of about 3.5 cm center-to-center (See, FIG. 1). This distance has been standard practice for the adult pad electrodes for respiratory monitoring and cardiac output monitoring by bioimpedance or bioreactance for many years. Other bioimpedance based devices that measure respiratory rate, pulse rate, and/or EKG also can be included in this consideration, with a particular distance chosen for a particular product for adult use. However, use of the current commercially available standard adult electrodes (device) is not feasible for small pediatric and neonatal/premature individuals due to torso size constraints. Through systematic research and design of a new pediatric pad set it was surprisingly discovered that decreasing the distance (B and C in FIG. 20) between corresponding source and sink electrodes had a profound impact on the impedance measurements by introducing parasitic impedance caused by direct current leakage between the sink and source electrodes. Electrode placement of the pair of electrodes (source-sense) that is too close increases the effect of parasitic impedance and reduces the fidelity (signal quality) of the measured trans-thoracic impedance. This, in turn, compromises the accuracy of not only the impedance measurement, but also the lung volumes calculated based on the measurement. The embodiment depicted in FIG. 20 been optimized based on the constraints created by patient or individual size, distance between electrodes, and electrode geometry. By optimizing these system design criteria, the device minimizes the interference caused by the parasitic impedance and provides an optimal trans-thoracic impedance signal for use in determining respiratory (lung) volumes. Similarly, this spacing is as important for other bioimpedance based systems such as cardiac output or body composition measurement systems.

Figure 20:
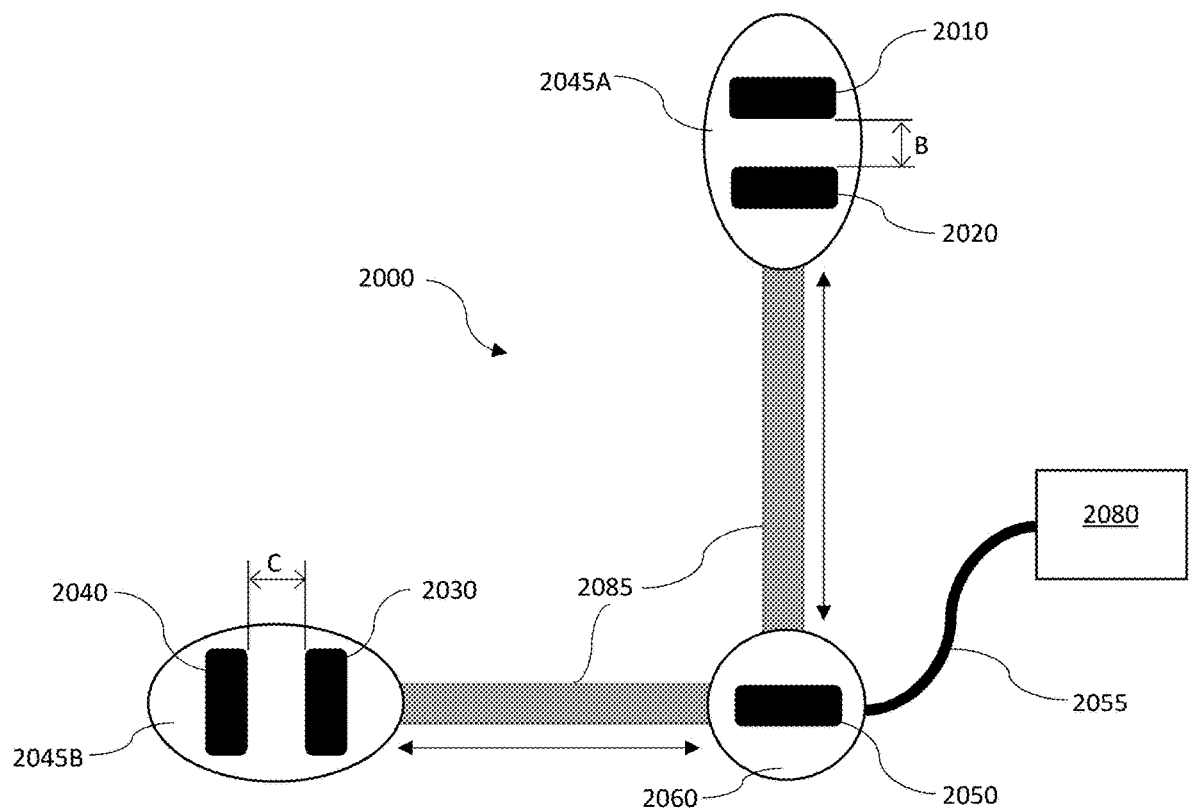
FIG. 20 depicts an embodiment of an electrode padset for use on a neonate.

FIG. 20 depicts an example of a padset 2000 for a neonate. Padset 2000 is preferably for use on neonates, premature babies, infants or pediatric individuals under 38 kg, 45 kg, 50 kg, or under another predetermined weight or height or torso length or another relevant parameter. Padset 2000 may also be useable on smaller body parts of adults, teenagers, and children, for example on arms or legs for other impedance applications. Additionally, padset 2000 may be used on small animals. Padset 2000 is similar to the padset shown in FIG. 1, however the components have been reduced in size for use on neonates. In a preferred embodiment, the padsets for a population within a certain set of size boundaries (i.e. height, weight, BSA, BMI) or other demographics (sex, age, etc) or body composition characteristics should have the same separation within an electrode pair, while the separation between the pairs may vary based on difference in size within the range.

Aspects of the invention relate to a medical measurement device (e.g., tetrapolar electrode padset, analysis software and accompanying circuitry) for sensing a physiological parameter (e.g., impedance, sourced current, induced voltage, and other parameters associated with a physiological system). In particular, the invention includes a plurality of electrodes with spacing between electrodes within an electrode pair that takes into account any of the following: size of patient, body composition, parasitic impedance, total impedance, change in impedance, change in impedance as a function of time (dZ/dt), to select or optimize impedance signal to improve the diagnostic impedance measure for patient treatment. In one embodiment, the electrodes or sensor elements are mounted at the end of a lead comprising a molded plastic substrate with electrically conductive paths connecting the measured signal to the accompanying circuitry. When deciding the spacing between electrodes in an electrode pair set, the introduction of parasitic or unknown impedance due to electrode placement needs to be accounted for. The interference from the parasitic impedance can be ameliorated by changing either the spacing between electrodes, the measurement system, or both. In one embodiment, the parasitic impedance is measured and if it is too high such that it reduces the signal-to-noise ratio below acceptable limits, the measurement system may report this to the user or the measurement system may stop displaying impedance measurements or secondary derived measurement such as lung volume. In another embodiment, the measurement system can adaptively compensate for the parasitic impedance and continue to display correct impedance data or secondary derived measurement. In one embodiment, spacing with measurable parasitic impedance may be chosen to achieve optimal anatomic placement with the measurement system designed to account for the parasitic component. In a preferred embodiment, the spacing is 10 mm between edges of the electrode hydrogel pads, which is associated with known parasitic impedance. A padset with this spacing is attached to a bioimpedance system that is designed to account for the parasitic impedance and still generates respiratory volume measurements with accuracy that is clinically relevant.

Padset 2000 preferably comprises a plurality of electrodes sized and shaped to fit on a pad support substrate 2045A and 2045B. In the illustrated embodiment, a first electrode pair 2010 and 2020 is separated by a distance B and a second electrode pair 2030 and 2040 is separated by a distance C. The distances B and C are preferably approximately equal but may differ without departing from the scope of the invention. In the preferred embodiment, distances B and C are measured from the inner edge of a first electrode to an inner edge of a corresponding electrode, as shown in FIG. 20. However, in other embodiments, the distances can be measured between center points of electrodes or between other points on the electrodes.

While the electrodes are depicted as rectangular, they may have another shape, for example, the electrodes may be circular or ovular, further reducing the edge-to-edge spacing without an increase in parasitic impedance. In such an embodiment, the minimized distance may not be the Euclidian distance between the edges of the electrodes, but rather the distance between their centroids or be a function of their moments of inertia. Additionally, the electrodes may all have the same shape or may have different shapes.

Figure 23:
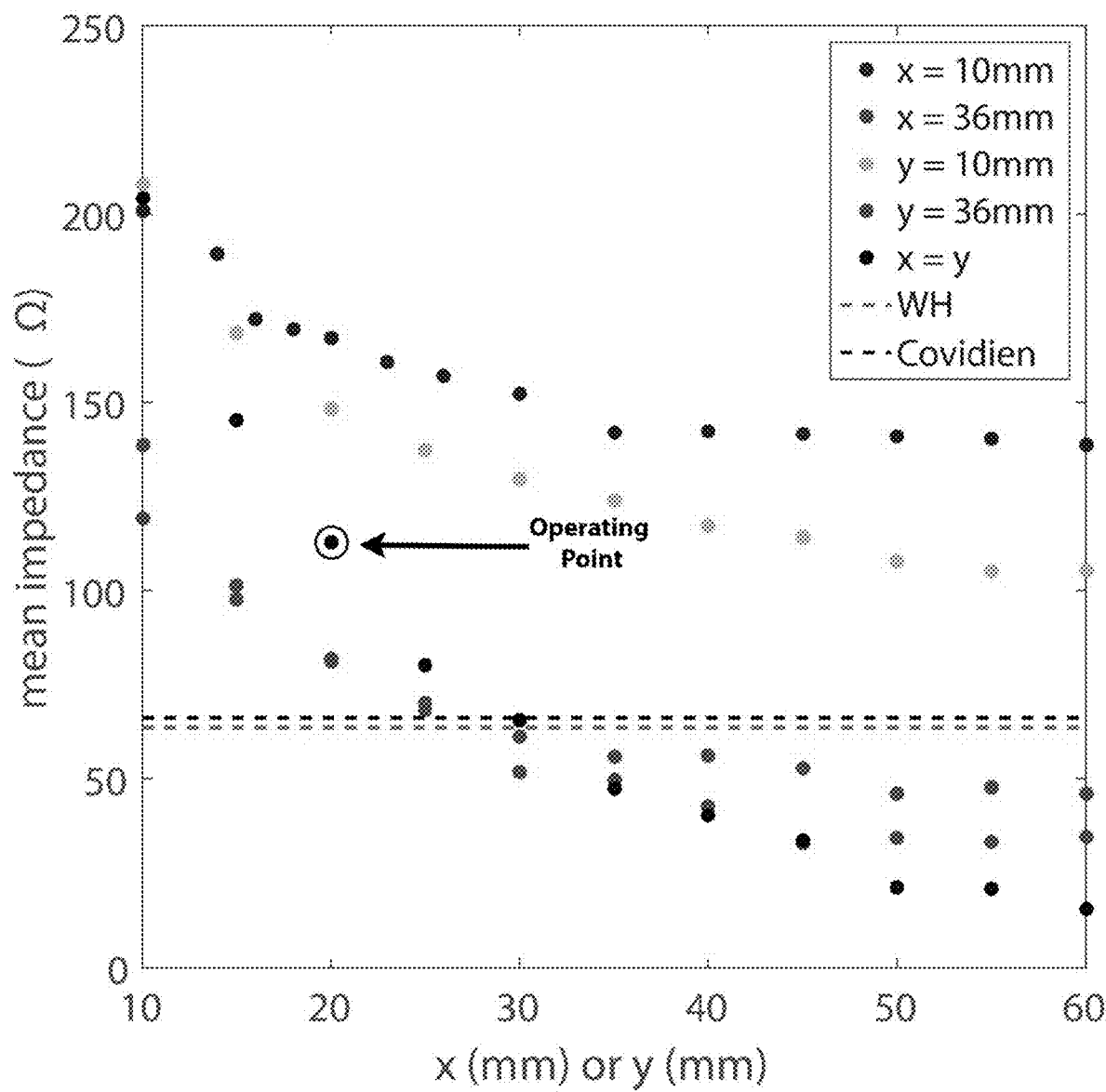
FIG. 23 depicts a graph of actual impedance testing on electrode spacing for various electrode geometries

Preferably, each electrode is about 2.54 cm by 0.9525 cm in size. However, the electrodes can range from 2 cm by 0.5 cm to 4 cm by 3 cm. The electrodes may all be the same size or may have different sizes. Preferably, distances B and C depend on the size of the electrodes, the size of the patient, the signal strength passed through the electrodes, or a combination thereof. For example, FIG. 23 depicts a graph of actual impedance testing on electrode spacing for various electrode geometries. As shown in the figure, the effects of the parasitic impedance effectively disappear when electrode separation exceeds about 35 mm. The algorithm and/or analysis required to process the impedance data to obtain volume data varies with the spacing between the electrodes of the electrode pairs. For very large individuals or for large animals, the optimal spacing between electrodes within an electrode pair may be larger than the standard adult placement FIG. 24 depicts an embodiment of the spacing of the electrodes. Distance between the lower sternum electrode and the xiphoid electrode are preferably adjustable from about 1-5.7 cm and the distance between the xiphoid and lateral torso electrodes are preferably adjustable between about 2-5 cm. Sink and source electrode pairs are preferably separated by 1 cm (+/−cm) edge-to-edge with a rectangular electrode geometry (e.g. distances B and C in FIG. 20).

Figure 21A:
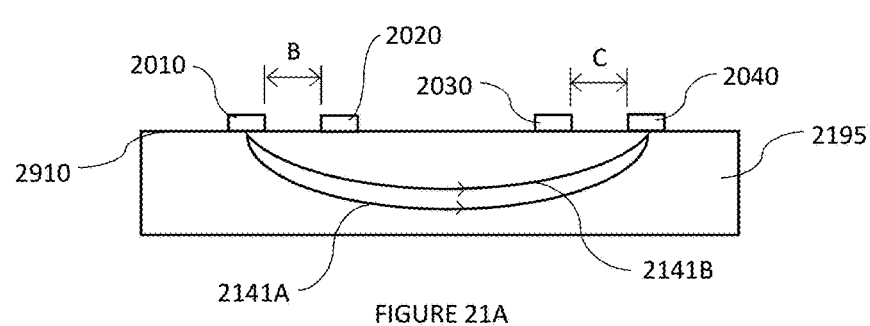
FIGS. 21A-B depict embodiments proper and improper separation of electrodes for the padset of FIG. 20.
Figure 21B:
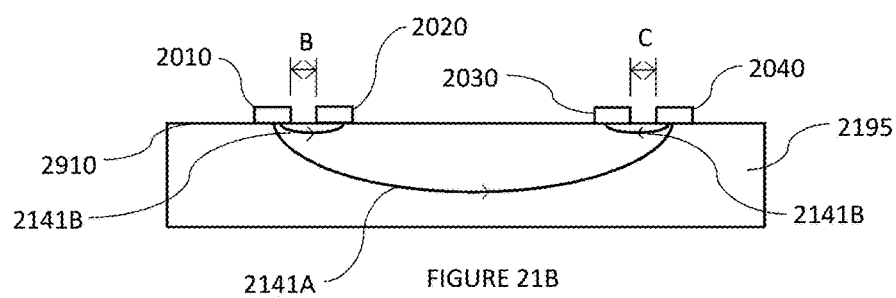

An electrode pair preferably is secured to the pad support substrate 2045A and 2045B on a first side, and on a second side is has an Ag/AgCl gel (or another conductive adhesive) that provides a signal pathway from the skin tissue into and out of an electrode, continuing along a signal pathway contained on the flexible substrate 2085 into the measuring unit 2080 via a hub 2060. FIGS. 21A and 21B depict the current flow through a patient when the electrodes are properly spaced and spaced too close together, respectively. Referring to FIG. 21A, current 2141A and 2141B flows through the patient's thorax cavity 2195 between the source electrode 2010 and sink electrode 2040. Provided the distances B and C are large enough, the supplied current 2141A and 2141B flows substantially through the thorax. The use of the tetrapolar configuration reduces, if not eliminates, skin tissue impedance 2190, so the calculated impedance Z, is a measure of a patient's trans-thoracic impedance.

Referring to FIG. 21B, reducing the distance B and/or C decreases current flow 2141A through the thorax region of the patient. It also presents the possibility of electrodes touching with patient motion and changes in skin conformation, or of changes in impedance due to water or sweat or other changes in surface impedance having a greater influence. The lost current 2414B travels between electrode pairs 2010 and 2020 as well as 2030 and 2040, increasing parasitic impedance, Z* and reducing the fraction of actual patient impedance within the overall measured impedance signal (i.e. decreasing the signal-to-noise ratio). This is manifested in reduced signal quality at the measuring system. Other ways of configuring the electrodes to measure impedance can be used without departing from the scope of the invention. For example, the electrode pairs can be placed side-by-side along the same line to measure the impedance of another body cavity or organ, or as an array of properly interconnected electrodes, instead of as show in FIG. 20.

Although described primarily in the context of a tetrapolar electrode arrangement, the present invention can be applied to a two electrode, or sets of n-electrode arrangements such as an array of electrodes applied to a patient's body. The invention is not limited to a human patient but may be used on an animal for which internal impedance is needed for monitoring of physiology or state of health or to provide a diagnosis.

Figure 22:
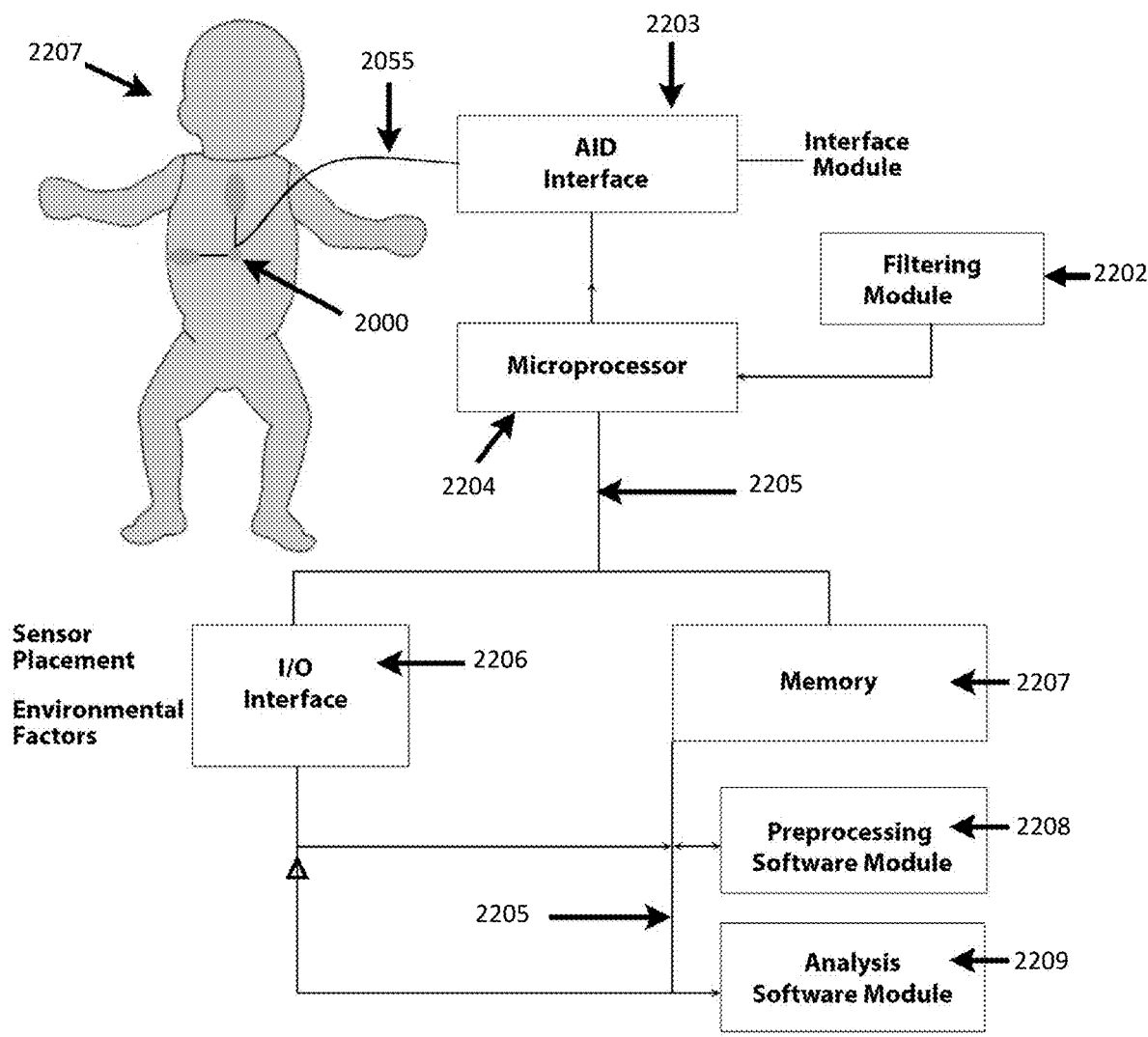
FIG. 22 depicts an embodiment of a system using the electrode padset on a neonate.

FIG. 22 depicts an embodiment of padset 2000 placed on a neonate 2207 and the attached patient measuring system 2080. The padset 2000 may be placed on different parts of the body than those shown in FIG. 22 to measure impedance of for example an organ or another body part without departing from the scope of this invention. The padset 2000 is connected via a conductive flexible cable 2055 to an interface module 2203 of the patient measuring system 2080. The system 2080 provides the source current to the patient 2207 and receives signals from the patient 2207 via cable 2055. The measuring system 2080 measures the induced voltage across electrodes 2020 and 2030, and calculates the impedance, Z.

The current and voltage signals are processed in and out of the measuring system 2080 using an analog/digital interface module 2203. The interface module 2203 communicates to a microprocessor 2204 that processes the incoming data such as parsing the data stream received at interface module 2203, separating out the measured sink current and induced voltage from overhead information such as checksum bits. The separated data or measurement payload is further processed or prepared by the microprocessor using a preprocessing software module 2208, directly used by the analysis software module 2209, or stored in memory 2207, such as RAM or ROM, for future use. The preprocessing software module may package the data into different format types or number systems for use by another part of the system.

Processed or incoming data, and user input is available through the input/output interface module (I/O module) 2206. A user can input patient information such as height, weight, sternal length, torso size or age via the interface module 2206. The interface module 2206 can be used to provide data from other medical devices or via a third-party device such as a cell phone or wireless network (not shown). This data may be used directly by the analysis software module 2209 or preprocessed using software module 2208. Data movement between the modules is over a data bus 2205 under control of a real-time operating system present on microprocessor 2204. Microprocessors based on the Ardunio™, Raspberry PI™ or STMicroelectronics™ STM32F107 family can be used without departing from the scope of this invention.

Figure 25:
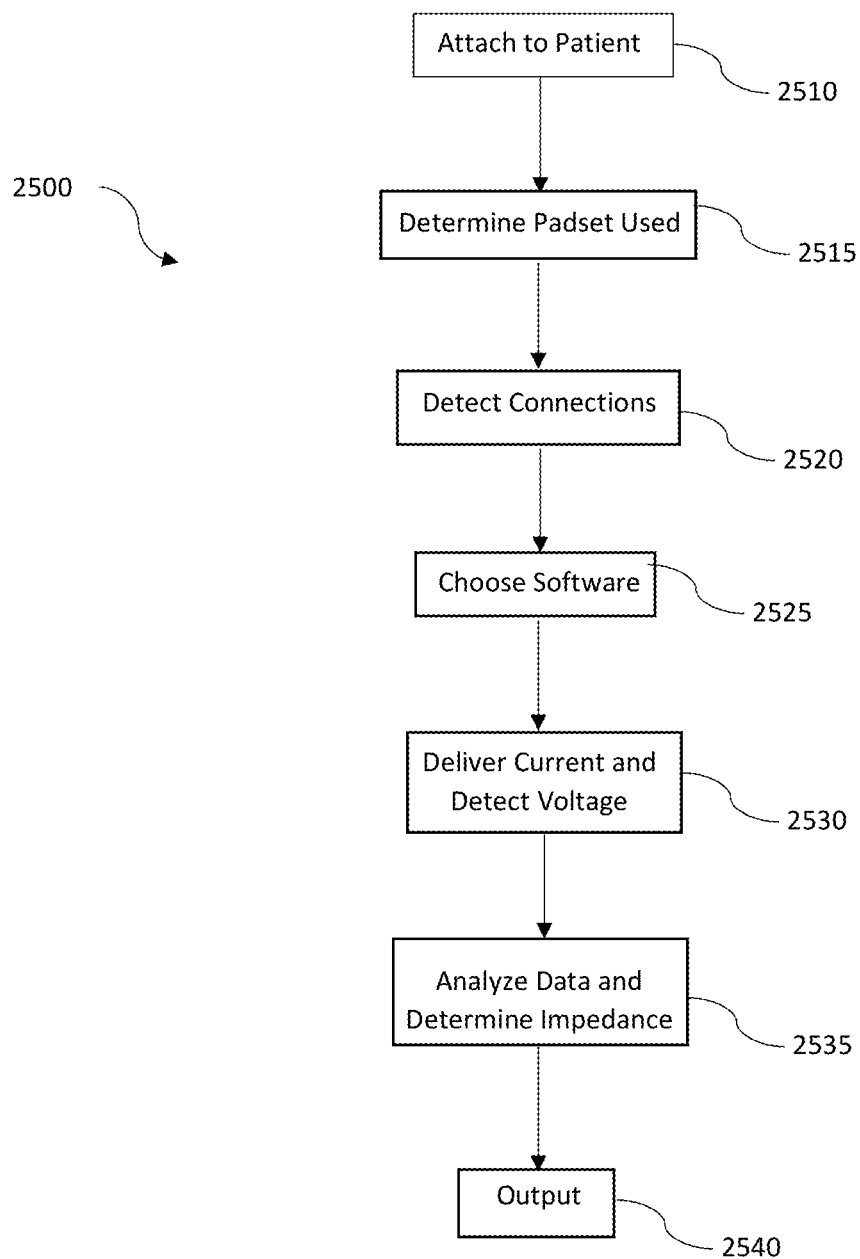
FIG. 25 depicts an embodiment of a method of analyzing a patient.

FIG. 25 is a flow chart of an embodiment of the method of analyzing a patient using the padsets described herein. Method 2500 preferably removes and/or reduces of the parasitic impedance, Z*, that distorts the real, measured patient impedance, Z. Since the parasitic impedance, Z*, degrades signal strength into the filtering module 2202, an adjustment is made by the analysis software module 2209. At step 2510, an appropriate sized padset is attached to the patient. For example, an adult padset is attached to an adult, a neonatal padset is attached to a baby, or an extra-large padset is attached to an obese person, with the adjustable portions adjust to place the electrodes at the desired positions on the patient.

At step 2515, once the padset is coupled to the measuring system, the measuring system preferably autodetects the padset used. In other embodiments, a technician may input the padset information. Depending on the measuring system's initial configuration, the user may confirm the electrode detected are attached to the patient. In one embodiment, the cable with a specific connector or an electrode padset/cable smart chip handshake or the characteristics of the bioimpedance signal is noted by the monitoring system to provide information of the specific electrode spacing, such as information whether an adult, large adult, neonatal, pediatric, premature infant, large animal padset is being used. The height and weight of the patient may be entered into the monitoring system and the system may suggest which padset to choose. In another embodiment, the technician inputs which specific padset with specific electrode spacing is chosen. The electrode spacing can be selected from a menu with range of spacings or by direct input by the medical practitioner. At step 2520 the system preferably preforms a check to determine if the padset is properly attached to the measuring system and all connections are working. This step ensures the circuit is complete before the measuring system sources current and measures the sink current and induced voltage. At step 2525 the system preferably chooses the appropriate software and/or algorithm to use with the padset currently coupled to the system. Each algorithm preferably takes into account any expected parasitic impedance, Z*, based on the configuration of the padset and adjusts the readings accordingly. For example, if the parasitic impedance is known, the algorithms can be programmed to "ignore" or remove the parasitic impedance from the signal. Preferably, the electrode spacing is defined apriori and the algorithms are programmed to adjust for the spacing. Preferably, there is a database that matches padsets to known parasitic impedances and the proper algorithm or correction coefficient to mitigate the parasitic impedance.

At step 2530, the system delivers source current via electrode an electrode and measures the induced voltage at a fixed frequency for a plurality of "n" samples. The system may be programmed to measure at a plurality of different frequencies without departing from the scope of the invention. At step 2035, the analysis software module receives input data over the data bus from one or more of the preprocessing software module, memory, or I/O interface module, and determines the impedance, Z, mean impedance, Zm, or change in impedance, ΔZ, from the "n" measured samples. At step 2535, there is an output. In a preferred embodiment, the output is a respiratory volume measurement such as tidal volume or minute volume and thereby can provide monitoring or diagnostic information to clinicians or individuals as to physiology or disease state, or can trigger an alarm or an alert for set parameters.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A system for measuring bioimpedance signals, comprising:
    an electrode padset selected from at least two different sized electrode padsets;
    a microprocessor coupled to the electrode padset in communication with and adapted to receive bioimpedance signals from the electrode padset, and to measure the bioimpedance of a patient;
    a data receiver coupled to the microprocessor; and
    software executing on the microprocessor, wherein the software:
        determines the size of the electrode padset based on data received by the microprocessor;
        determines a known parasitic impedance based on the electrode padset that was selected; and
        mitigates the known parasitic impedance of the electrode padset;
    wherein the electrode padset comprises:
        at least two thoracic electrode pads, each thoracic electrode pad having a pair of electrodes; and
        an electrically conductive material coupling at least one thoracic electrode pad to at least one other thoracic electrode pad.

2. The system of claim 1, wherein each thoracic electrode pad has a known distance between the pairs of electrodes.

3. The system of claim 2, wherein the distance is at least 35 mm.

4. The system of claim 1, wherein the software executing on the microprocessor is adapted to automatically determine which-electrode padsets is in communication with the microprocessor.

5. The system of claim 1, wherein the microprocessor determines a level of parasitic impedance and at least one of reports the determined level of parasitic impedance and does not display either impedance measurements or secondary derived impedance measurements.

6. The system of claim 1, wherein the microprocessor outputs respiratory volume measurements.

7. The system of claim 1, wherein at least one electrode padset is adapted to fit a neonate.

8. The system of claim 1, wherein each electrode padset is one of directly coupled to the microprocessor or is in wireless communication with the microprocessor.

9. The system of claim 1, wherein each electrode padset is a single unit.

10. The system of claim 1, wherein each electrode padset is adapted to acquire at least one of electrical bioimpedance (thoracic or cardiac), electrocardiogramalectroencephalography (EEG), and electromyography (EMG) signals.

11. The system of claim 1, wherein each electrode padset is adapted to acquire at least one channel of tetrapolar transthoracic bioimpedance signals.

12. The system of claim 11, wherein there are at least two bioimpedance channels and the bioimpedance channels are oriented at an angle between 0 and 90 degrees to each other.

13. The system of claim 1, wherein each electrode padset is adapted to acquire a bilateral transthoracic bioimpedance signal.

14. The system of claim 1, wherein each electrode padset further comprises a memory chip adapted to transmit data to the data receiver.

15. The system of claim 14, wherein the memory chip stores at least one of calibration data, production data, patient data, expiration date data, and electrode padset data.

16. The system of claim 14, wherein the memory chip is capable of wireless communication.

17. The system of claim 14, wherein memory chip is passive or is active and couplable to an internal or external power supply.

18. The system of claim 1, wherein the data receiver is an input device and the size of the electrode padset coupled to the microprocessor is input by a user.

19. A method of obtaining a bioimpedance signal, comprising:
- selecting an electrode padset from at least two different sized electrode padsets for use on a patient, wherein each sized electrode padset has a known parasitic impedance;
- coupling the selected electrode padset to a microprocessor and the patient;
- executing software on the microprocessor, wherein the software is adapted to remove the parasitic impedance of the selected electrode padset based on the selected electrode padset's geometry;
- delivering a current to the patient via the selected electrode padset;
- receiving the current from the patient via the selected electrode padset;
- filtering out the parasitic impedance;
- determining the impedance of the patient;
- calculating at least one respiratory volume measurement of the patient; and
- outputting the at least one respiratory volume measurement of the patient.

20. The method of claim 19, wherein the microprocessor autodectects the selected padset.

21. The method of claim 19, further comprising informing the microprocessor of the selected padset.

22. The method of claim 19, further comprising inputting patient information into the microprocessor.

23. The method of claim 19, wherein each respiratory volume measurement is one of tidal volume or minute volume.

24. The method of claim 19, wherein each padset is comprised of:
- a pair of sternal electrodes;
- a pair of side electrodes;
- a xiphoid electrode; and
- an electrically conductive material coupling the pair of sternal electrodes and the pair of side electrodes to the xiphoid electrode.

25. The method of claim 24, wherein the padset's geometry comprises a first distance between the pair of sternal electrodes and a second distance between the pair of side electrodes.

26. The method of claim 19, wherein each padset is adapted to fit a neonate.

27. The method of claim 19, wherein each padset is one of directly coupled to the microprocessor or is in wireless communication with the microprocessor.

28. The method of claim 19, wherein each padset is a single unit.

29. The method of claim 19, wherein each padset is adapted to acquire at least one of electrical bioimpedance (thoracic or cardiac), electrocardiography (ECG), electroencephalography (EEG), and electromyography (EMG) signals.

30. The method of claim 19, wherein each padset is adapted to acquire at least one channel of tetrapolar transthoracic bioimpedance signals.

31. The method of claim 30, wherein there are at least two bioimpedance channels and the bioimpedance channels are oriented at an angle between 0 and 90 degrees to each other.

32. The method of claim 19, wherein each padset is adapted to acquire a bilateral transthoracic bioimpedance signal.

33. The method of claim 19, wherein each padset comprises a memory chip.

34. The method of claim 33, wherein the memory chip stores at least one of calibration data, production data, patient data, expiration date data, and padset data.

35. The method of claim 33, wherein the memory chip is capable of wireless communication.

36. The method of claim 33, wherein memory chip is passive and is couplable to an internal or external power supply.

* * * * *